(12) United States Patent
Choi et al.

(10) Patent No.: US 9,243,012 B2
(45) Date of Patent: Jan. 26, 2016

(54) PHOSPHOROUS CONTAINING BENZOXAZINE-BASED MONOMER, OR POLYMER THEREOF

(75) Inventors: Seongwoo Choi, Yongin-si (KR); Jungock Park, Yongin-si (KR); Wonmok Lee, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 432 days.

(21) Appl. No.: 13/478,893

(22) Filed: May 23, 2012

(65) Prior Publication Data

US 2012/0264909 A1 Oct. 18, 2012

Related U.S. Application Data

(62) Division of application No. 12/208,492, filed on Sep. 11, 2008, now Pat. No. 8,192,892.

(30) Foreign Application Priority Data

Sep. 11, 2007 (KR) ................................ 2007-92145

(51) Int. Cl.

| | |
|---|---|
| C08G 79/04 | (2006.01) |
| C07D 413/14 | (2006.01) |
| C07F 9/6533 | (2006.01) |
| C07F 9/6558 | (2006.01) |
| C08J 5/22 | (2006.01) |
| H01M 4/86 | (2006.01) |
| H01M 4/90 | (2006.01) |
| H01M 4/92 | (2006.01) |
| H01M 8/10 | (2006.01) |

(52) U.S. Cl.
CPC ......... *C07F 9/65335* (2013.01); *C07F 9/65583* (2013.01); *C08J 5/2256* (2013.01); *H01M 4/8605* (2013.01); *H01M 4/8652* (2013.01); *H01M 4/9008* (2013.01); *H01M 4/921* (2013.01); *H01M 8/103* (2013.01); *H01M 8/1027* (2013.01); *H01M 8/1034* (2013.01); *H01M 8/1039* (2013.01); *H01M 8/1048* (2013.01); *H01M 8/1072* (2013.01); *C08J 2379/06* (2013.01); *H01M 2300/0082* (2013.01); *H01M 2300/0091* (2013.01); *Y02E 60/521* (2013.01)

(58) Field of Classification Search
CPC .............. C07F 9/65335; C07F 9/65583; C08J 2379/06; C08J 5/2256; H01M 2300/0082; H01M 2300/0091; H01M 4/8605; H01M 4/8652; H01M 4/9008; H01M 4/921; H01M 8/1027; H01M 8/103; H01M 8/1034; H01M 8/1039; H01M 8/1048; H01M 8/1072; Y02E 60/521
USPC ......... 429/479, 484, 485, 487, 523, 524–529; 544/73, 90; 528/399
See application file for complete search history.

(56) References Cited

U.S. PATENT DOCUMENTS

| | | |
|---|---|---|
| 4,828,699 A | 5/1989 | Soehngen |
| 5,098,985 A | 3/1992 | Harris et al. |
| 5,250,633 A | 10/1993 | Calundann et al. |
| 5,410,012 A | 4/1995 | Connell et al. |
| 5,637,670 A | 6/1997 | Connell et al. |
| 5,945,233 A | 8/1999 | Onorato et al. |
| 6,042,968 A | 3/2000 | Onorato et al. |
| 6,482,946 B1 | 11/2002 | Dettloff et al. |
| 6,620,905 B1 | 9/2003 | Musa |
| 6,855,674 B2 | 2/2005 | Gutierrez |
| 7,094,490 B2 | 8/2006 | Cao et al. |
| 7,157,509 B2 | 1/2007 | Li et al. |
| 7,371,480 B2 | 5/2008 | Ono et al. |
| 7,388,035 B2 | 6/2008 | Kim et al. |
| 7,405,021 B2 | 7/2008 | Gascoyne et al. |
| 7,510,678 B2 | 3/2009 | Kim et al. |
| 7,619,044 B2 | 11/2009 | Lee et al. |
| 7,649,025 B2 | 1/2010 | Kitamura et al. |
| 7,709,579 B2 | 5/2010 | Lehmann et al. |
| 2001/0041283 A1 | 11/2001 | Hitomi |
| 2002/0127474 A1 | 9/2002 | Fleischer et al. |
| 2002/0164516 A1 | 11/2002 | Hasegawa et al. |
| 2003/0190516 A1 | 10/2003 | Tanno |
| 2004/0005493 A1 | 1/2004 | Tanno |
| 2004/0028976 A1 | 2/2004 | Cabasso et al. |
| 2004/0206953 A1 | 10/2004 | Morena et al. |
| 2004/0231143 A1 | 11/2004 | Visco et al. |
| 2004/0241522 A1 | 12/2004 | Ono et al. |
| 2004/0261660 A1 | 12/2004 | Li et al. |
| 2005/0074651 A1 | 4/2005 | Kidai et al. |
| 2005/0084728 A1 | 4/2005 | Kim et al. |
| 2005/0089744 A1 | 4/2005 | Kim et al. |
| 2005/0130006 A1 | 6/2005 | Hoshi et al. |
| 2005/0142413 A1 | 6/2005 | Kimura et al. |

(Continued)

FOREIGN PATENT DOCUMENTS

| | | |
|---|---|---|
| CN | 101220153 | 7/2008 |
| DE | 2034 887 | 1/1972 |

(Continued)

OTHER PUBLICATIONS

U.S. Office Action dated Jun. 22, 2009, issued in corresponding U.S. Appl. No. 11/947,011.
U.S. Office Action dated Sep. 3, 2009, issued in corresponding U.S. Appl. No. 11/743,778.
U.S. Office Action dated Sep. 8, 2009, issued in corresponding U.S. Appl. No. 11/765,033.
U.S. Office Action dated Jun. 1, 2010, issued in corresponding U.S. Appl. No. 11/765,056.

(Continued)

*Primary Examiner* — Carlos Barcena
(74) *Attorney, Agent, or Firm* — Stein IP, LLC

(57) ABSTRACT

A phosphorous containing benzoxazine-based monomer, or a polymer thereof.

7 Claims, 14 Drawing Sheets

(56) References Cited

U.S. PATENT DOCUMENTS

| | | | |
|---|---|---|---|
| 2005/0247908 A1 | 11/2005 | Keller et al. |
| 2006/0078774 A1 | 4/2006 | Uensal et al. |
| 2006/0241192 A1 | 10/2006 | Kitamura et al. |
| 2007/0020507 A1 | 1/2007 | Kim et al. |
| 2007/0141426 A1 | 6/2007 | Choi et al. |
| 2007/0184323 A1 | 8/2007 | Lee et al. |
| 2007/0200994 A1 | 8/2007 | Yanagisawa |
| 2007/0238723 A1 | 10/2007 | Goble et al. |
| 2007/0275285 A1 | 11/2007 | Choi et al. |
| 2008/0020264 A1 | 1/2008 | Sun et al. |
| 2008/0045688 A1 | 2/2008 | Lin et al. |
| 2008/0050633 A1 | 2/2008 | Kwon et al. |
| 2008/0118817 A1 | 5/2008 | Lee et al. |
| 2008/0145743 A1 | 6/2008 | Choi et al. |
| 2008/0157422 A1 | 7/2008 | Lee et al. |
| 2009/0075147 A1 | 3/2009 | Kitamura et al. |
| 2009/0117436 A1 | 5/2009 | Choi et al. |
| 2009/0117440 A1 | 5/2009 | Choi et al. |
| 2010/0273087 A1 | 10/2010 | Choi et al. |
| 2011/0189581 A1 | 8/2011 | Choi et al. |

FOREIGN PATENT DOCUMENTS

| | | |
|---|---|---|
| DE | 603 02 673 | 8/2006 |
| EP | 1 247 844 | 10/2002 |
| EP | 1 253 661 | 10/2002 |
| EP | 1 760 110 | 3/2007 |
| EP | 1 881 549 | 1/2008 |
| JP | 10-25343 | 1/1998 |
| JP | 11-503262 | 3/1999 |
| JP | 11-97011 | 4/1999 |
| JP | 2001-19844 | 1/2001 |
| JP | 2001-270891 | 10/2001 |
| JP | 2001-271070 | 10/2001 |
| JP | 2002-260682 | 9/2002 |
| JP | 2003-12747 | 1/2003 |
| JP | 2003-12924 | 1/2003 |
| JP | 2003-286320 | 10/2003 |
| JP | 2003-327694 | 11/2003 |
| JP | 2004-43547 | 2/2004 |
| JP | 2004-103494 | 4/2004 |
| JP | 2004-149779 | 5/2004 |
| JP | 2004-179514 | 6/2004 |
| JP | 2005-41936 | 2/2005 |
| JP | 2005-82690 | 3/2005 |
| JP | 2005-283082 | 10/2005 |
| JP | 2006-339065 | 12/2006 |
| JP | 2007-70631 | 3/2007 |
| JP | 2007-214108 | 8/2007 |
| KR | 10-2006-0011831 | 2/2006 |
| KR | 10-2006-0055291 | 5/2006 |
| KR | 10-2007-0025626 | 3/2007 |
| KR | 10-2007-0025627 | 3/2007 |
| KR | 10-0745741 | 7/2007 |
| KR | 10-2007-0102579 | 10/2007 |
| WO | WO 96/13872 | 5/1996 |
| WO | WO 02/14334 | 2/2002 |
| WO | WO 02/057279 | 7/2002 |
| WO | WO 03/072638 | 9/2003 |
| WO | WO 2004/009708 | 1/2004 |
| WO | WO 2004/101509 | 11/2004 |
| WO | WO 2005/000955 | 1/2005 |
| WO | WO 2006/132207 | 12/2006 |

OTHER PUBLICATIONS

U.S. Office Action dated Jan. 8, 2010, issued in corresponding U.S. Appl. No. 11/514,254.
U.S. Office Action dated Jan. 15, 2010, issued in corresponding U.S. Appl. No. 11/947,011.
U.S. Office Action dated Feb. 19, 2010, issued in corresponding U.S. Appl. No. 11/743,778.
U.S. Office Action dated Mar. 30, 2010, issued in corresponding U.S. Appl. No. 11/947,011.
U.S. Office Action dated May 6, 2010, issued in corresponding U.S. Appl. No. 11/514,254.
U.S. Office Action dated Jun. 17, 2010, issued in corresponding U.S. Appl. No. 11/765,033.
U.S. Office Action dated Jul. 11, 2011, issued in corresponding U.S. Appl. No. 12/208,492.
U.S. Office Action dated Aug. 11, 2011, issued in corresponding U.S. Appl. No. 12/247,338.
U.S. Office Action dated Aug. 18, 2011, issued in corresponding U.S. Appl. No. 12/266,039.
U.S. Office Action dated Sep. 2, 2011, issued in corresponding U.S. Appl. No. 12/262,854.
U.S. Office Action dated Sep. 12, 2011, issued in corresponding U.S. Appl. No. 12/263,011.
U.S. Office Action dated Nov. 14, 2011, issued in corresponding U.S. Appl. No. 12/208,492.
U.S. Office Action dated Dec. 12, 2011, issued in corresponding U.S. Appl. No. 12/263,011.
U.S. Office Action dated Dec. 22, 2011, issued in corresponding U.S. Appl. No. 12/247,338.
U.S. Office Action dated Jan. 20, 2012, issued in corresponding U.S. Appl. No. 11/947,011.
U.S. Notice of Allowance dated Jan. 31, 2012, issued in corresponding U.S. Appl. No. 12/266,039.
U.S. Office Action dated Feb. 2, 2012, issued in corresponding U.S. Appl. No. 12/208,664.
U.S. Notice of Allowance dated Feb. 3, 2012, issued in corresponding U.S. Appl. No. 12/208,492.
U.S. Notice of Allowance dated Feb. 3, 2012, issued in corresponding U.S. Appl. No. 12/262,854.
U.S. Notice of Allowance dated Mar. 14, 2012, issued in corresponding U.S. Appl. No. 12/263,011.
U.S. Notice of Allowability dated Mar. 22, 2012, issued in corresponding U.S. Appl. No. 12/263,011.
U.S. Office Action dated Apr. 26, 2012, issued in corresponding U.S. Appl. No. 11/947,011.
U.S. Office Action dated May 10, 2012, issued in corresponding U.S. Appl. No. 12/247,338.
U.S. Notice of Allowance dated Jul. 11, 2012, issued in corresponding U.S. Appl. No. 12/247,338.
Seong-Woo Choi et al., "Synthesis, characterization and thermal degradation of functional benzoxazine monomers and polymers containing phenylphosphine oxide", Polymer Degradation and Stability 91 (2006), pp. 1166-1178.
Seong-Woo Choi, et al., Polybenzoxazine Based Membrane with Enhanced Oxygen Permeability Inducing Fluorine Containing Benzoxazine Monomer as an Electrode Additive and Binder for High Temperature PEM Fuel Cells; slides of presentation at 212th ECS, Washington, DC, Oct. 9, 2007.
STN Registry database entries for RN 35141-82-3, RN 35141-83-4 and RN 35141-84-5, Database entry date Nov. 16, 1984. Accessed Jan. 26, 2012.
Tarek Agag, Journal of Applied Polymer Science, vol. 100, pp. 3769-3777 (2006).
212th ECS Meeting—Washington DC, Oct. 7-12, 2007, Program Information, B10—Proton Exchange Membrane Fuel Cells (PEMFC 7) Energy Technology/Physical and Analytical Electrochemistry/Battery/Industrial Electrochemistry and Electrochemical Engineering.
B. Antalek. "Using Pulsed Gradient Spin Echo NMR for Chemical Mixture Analysis: How to Obtain Optimum Results.", Concepts in Magnetic Resonance (2002) vol. 14(4), pp. 225-258.
S. Viel et al. "Diffusion-Ordered NMR Spectroscopy: A Versatile Tool for the Molecular Weight Determination of Uncharged Polysaccharides.", Biomacromolecules (2003) vol. 4, pp. 1843-1847.
D. A. Jayawickrama et al. "Polymer additives mixture analysis using pulsed-field gradient NMR spectroscopy.", Magn.Reson. Chem (1998), vol. 36, pp. 755-760.
K. Nishinari et al. " Soulution Properties of Pullulan.", Macromolecules (1991) vol. 24, pp. 5590-5593.
L.C. Van Gorkom et al. "Analysis of DOSY and GPC-NMR Experiments on Polymers by Multivariate Curve Resolution.", Journal of Magnetic Resonance (1998) vol. 130, pp. 125-130.

(56) References Cited

OTHER PUBLICATIONS

A. Chen et al. "Determination of Molecular Weight Distributions for Polymers by Diffusion-Ordered NMR.", J. Am. Chem. Soc. (1995) vol. 117, pp. 7965-7970.
Hajime Kimura et al. "Epoxy Resin Cured by Bisphenol a Based Benzoxazine.", Journal of Applied Polymer Science (1998), vol. 68, pp. 1903-1910.
Schuster, Martin F.H., et al., "Anhydrous Proton-Conducting Polymers", Annu. Rev. Mater. Res., vol. 33, 2003, pp. 233-261.
Yamada, M. et al., "Anhydrous proton conducting polymer electrolytes based on poly(vinylphosphonic acid)-heterocyclic composite material", Polymer, vol. 46, No. 9, 2005, pp. 2986-2992.
Pu, H., et al., "Proton Transport in Polybenzimidazole Blended with $H_3PO_4$ or $H_2SO_4$", J. Polymer Science, Part B: Polymer Physics, vol. 40, 2002, pp. 663-669.
Kim, Hyoung-Juhn et al. *Polybenzimidazoles for High Temperature Fuel Cell Application*. Macromol. Rapid Commun. 2004, vol. 25, pp. 1410-1413.
Ueda, Mitsuru et al. *Poly(benzimidazole) Synthesis by Direct Reaction of Methoxyphthalic Acids and Tetramine*. J. Poly. Sci. Part A: Polym. Chem, 27 pp. 2815-2818 (1989).
Choi et al., "Synthesis, characterization and thermal degradation of functional benzoxazine monomers and polymers containing phenylphosphine oxide", Polymer Degradation and Stability, vol. 91, No. 5, May 1, 2006, pp. 1166-1178.
Low, Hong Yee, et al. "Structural Effects of Phenols on the Thermal and Thermo-oxidative Degradation of Polybenzoxazines". Polymer, vol. 40, No. 15. Jul. 1999. pp. 4365-4376.
Kim, H.J., et al. "Synthesis and Thermal Characterization of Polybenzoxazines Based on Acetylene-functional Monomers". Polymer, vol. 40, No. 23. Nov. 1999. pp. 6565-6573.
Shen, Shyan Bob, et al. "Synthesis and Characterization of Polyfunctional Naphthoxazines and Related Polymers". Journal of Applied Polymer Science vol. 61, No. 9. 1996, pp. 1595-1605.
Lin et al., "Synthesis and Properties of Flame-Retardant Benzoxazines by Three Approaches", Journal of Polymer Science, Part A: Polymer Chemistry, vol. 44, 2006, pp. 3454-3468.
Hirai et al., "Air-Induced *anti*-Markovnikov Addition of Secondary Phosphine Oxides and H-Phosphinates to Alkenes", National Institute of Advanced Industrial Science and Technology, Organic Letters 2007, vol. 9, No. 1, pp. 53-55.
Beletskaya et al., "Arylation of 6*H*-Dibenzo[c,e][1,2 $\lambda^5$]oxaphosphinine 6-Oxide", Russian Journal of Organic Chemistry, vol. 40, No. 12, 2004, pp. 1782-1786.
Yamada et al., "A Novel Synthesis of 6-Hydroxyalkyl- and 6-Hydroxy-aralkyl-6*H*-dibenz[c,e][1,2]oxaphosphorin 6-Oxides", vol. 27, 1990, pp. 845-850.
Human translation of JP 2003-286320, A. Takeichi et al., Oct. 2003.
Human translation of JP 2004-103494, Kimura et al., Apr. 2004.
Machine translation of JP 2004-149779, Sakaguchi et al., May 2004.
European Search Report issued in European Patent Application No. 06254551.2-2115 on Nov. 21, 2006.
European Office Action issued in corresponding European Patent Application No. 07250814.6 on Oct. 30, 2007.
European Search Report issued in European Patent Application No. 08104319.2 on Oct. 13, 2008.
European Search Report issued in European Patent Application No. 08157494.9 on Nov. 24, 2008.
European Office Action dated Dec. 4, 2008, issued in corresponding European Patent Application No. 08164095.5.
European Search Report issued in European Patent Application No. 08164096.3 on Jan. 20, 2009.
European Search Report issued in European Patent Application No. 08166328.8 on Jan. 22, 2009.
European Search Report issued in European Patent Application No. 08168081.1 on Jan. 28, 2009.
Extended European Search Report issued in European Patent Application No. 08168032.4 on Feb. 3, 2009.
European Search Report issued in European Patent Application No. 08168404.5 on Feb. 10, 2009.
Extended European Search Report issued in European Patent Application No. 08168404.5 on Apr. 23, 2009.
European Search Report dated Jul. 21, 2010 issued in corresponding European Patent Application No. 10164784.0.
European Search Report dated Jul. 21, 2010 issued in corresponding European Patent Application No. 10164785.7.
Japanese Office Action issued in Japanese Patent Application No. 2006-239572 on Feb. 17, 2009.
Japanese Office Action dated Jun. 21, 2011, issued in corresponding Japanese Patent Application No. 2007-309320.
Japanese Office Action dated Sep. 20, 2011, issued in corresponding Japanese Patent Application No. 2008-233675.
Japanese Office Action dated Oct. 23, 2011, issued in corresponding Japanese Patent Application No. 2007-309320.
Korean Office Action dated Jul. 21, 2010, issued in corresponding Korean Patent Application No. 10-2008-0089999.
Korean Office Action dated Oct. 6, 2010, issued in corresponding Korean Patent Application No. 10-2008-0099549.
U.S. Appl. No. 11/514,254, filed Sep. 1, 2006, Seong-woo Choi et al., Samsung SDI Co., Ltd.
U.S. Appl. No. 11/514,831, filed Sep. 5, 2006, Seong-woo Choi et al., Samsung SDI Co., Ltd.
U.S. Appl. No. 11/743,778, filed May 3, 2007, Seong-woo Choi et al., Samsung SDI Co., Ltd.
U.S. Appl. No. 11/856,350, filed Sep. 17, 2007, Seong-woo Choi et al., Samsung SDI Co., Ltd.
U.S. Appl. No. 11/947,011, filed Nov. 29, 2007, Seong-woo Choi et al., Samsung Electronics Co., Ltd.
U.S. Appl. No. 12/208,492, filed Sep. 11, 2008, Seong-woo Choi et al., Samsung Electronics Co., Ltd.
U.S. Appl. No. 12/208,664, filed Sep. 11, 2008, Seong-woo Choi et al., Samsung Electronics Co., Ltd.
U.S. Appl. No. 11/765,033, filed Jun. 19, 2007, Hee-young Sun et al., Samsung SDI Co., Ltd.
U.S. Appl. No. 11/765,056, filed Jun. 19, 2007, Kyung-jung Kwon et al., Samsung SDI Co., Ltd.
U.S. Appl. No. 12/247,338, filed Oct. 8, 2008, Seong-woo Choi et al., Samsung Electronics Co., Ltd.
U.S. Appl. No. 12/263,011, filed Oct. 31, 2008, Seong-woo Choi et al., Samsung Electronics Co., Ltd.
U.S. Appl. No. 12/262,854, filed Oct. 31, 2008, Seong-woo Choi et al., Samsung Electronics Co., Ltd.
U.S. Appl. No. 12/266,039, filed Nov. 6, 2008, Seong-woo Choi et al., Samsung Electronics Co., Ltd.
U.S. Appl. No. 13/464,517, filed May 4, 2012, Seong-woo Choi et al., Samsung Electronics Co., Ltd.
U.S. Appl. No. 13/466,750, filed May 8, 2012, Seong-woo Choi et al., Samsung Electronics Co., Ltd.
U.S. Appl. No. 13/466,843, filed May 8, 2012, Seong-woo Choi et al., Samsung Electronics Co., Ltd.
U.S. Appl. No. 13/523,516, filed Jun. 14, 2012, Seong-woo Choi et al., Samsung Electronics Co., Ltd.
U.S. Appl. No. 13/560,321, filed Jul. 27, 2012, Seong-woo Choi et al., Samsung Electronics Co., Ltd.

PHOSPHOROUS CONTAINING BENZOXAZINE-BASED MONOMER, OR POLYMER THEREOF

CROSS-REFERENCE TO RELATED APPLICATIONS

This is a divisional of U.S. Application Ser. No. 12/208,492, filed Sep. 11, 2008, now U.S. Pat. No. 8,192,892, which claims the benefit of Korean Patent Application No. 10-2007-92145, filed on Sep. 11, 2007, in the Korean Intellectual Property Office, the disclosures of which are incorporated herein by reference.

BACKGROUND OF THE INVENTION

1. Field of the Invention

Aspects of the present invention relate to a phosphorous containing benzoxazine-based monomer, a polymer thereof, an electrode for a fuel cell including the same, an electrolyte membrane for a fuel cell including the same, and a fuel cell employing the same.

2. Description of the Related Art

Fuel cells using a polymer electrolyte membrane as an electrolyte, which operate at a relatively low temperature and can be miniaturized, are regarded as an alternative power source for automobiles and for residential distributed power generation systems. A known polymer electrolyte membrane used in polymer electrolyte membrane fuel cells is a perfluorocarbonsulfonic acid polymer represented by Nafion™.

However, these polymer electrolyte membranes typically must be hydrated to retain proton conductivity. In addition, a fuel cell system typically operates at 100° C. or higher in order to improve the system efficiency. However, the electrolyte membrane may not function well as a solid electrolyte at such a high temperature since moisture evaporates from the electrolyte membrane.

A non-hydrated electrolyte membrane that can be operated at 100° C. or higher has been developed in order to overcome these problems. For example, polybenzimidazole doped with phosphoric acid as a material used to form a non-hydrated electrolyte membrane is disclosed in U.S. Pat. No. 5,525,436.

In addition, in fuel cells using a perfluorocarbonsulfonic acid polymer membrane which operates at a low-temperature, an electrode having hydrophobicity by being mixed with water-repellent polytetrafluoroethylene (PTFE) is used in order to improve gas diffusion, since gas is blocked by water generated in a cathode (Japanese Patent Laid-Open Publication No. hei 05-283082).

Phosphoric acid fuel cells that operate at a high temperature (150-200° C.) use phosphoric acid in a liquid state as an electrolyte. However, a large amount of the liquid state phosphoric acid in an electrolyte inhibits gas diffusion within the electrode. Thus, an electrode catalyst layer that prevents pores of the electrode from being blocked by the phosphoric acid by mixing the electrode catalyst with polytetrafluoroethylene (PTFE) having water repellency has been used.

In fuel cells applying polybenzimidazole (PBI) retaining phosphoric acid, which is a high-temperature non-hydrated electrolyte, to an electrolyte membrane, attempts to impregnate an electrode with a liquid state phosphoric acid have been made and attempts to increase the loading amount of a metal catalyst have been made in order to facilitate interface contact between the electrode and the membrane. These attempts, however, did not sufficiently improve characteristics of the fuel cells.

When air is supplied to a cathode, aging takes about a week even if an electrode composition is optimized in a solid polymer electrolyte membrane doped with phosphoric acid. Although a fuel cell can have improved efficiency and aging time can be decreased by replacing air with oxygen, use of oxygen is not desirable for commercialization. Furthermore, an electrolyte membrane prepared using a homopolymer of PBI does not have sufficient mechanical properties, chemical stability, and capacity of phosphoric acid at a high temperature.

SUMMARY OF THE INVENTION

Aspects of the present invention provide a phosphorous containing benzoxazine-based monomer having excellent thermal, resistance and high phosphoric acid resistance, a polymer thereof, an electrode for a fuel cell including the same, an electrolyte membrane for a fuel cell including the same, and a fuel cell employing the same.

According to an embodiment of the present invention, there is provided a phosphorous containing benzoxazine-based monomer represented by Formula 1 below.

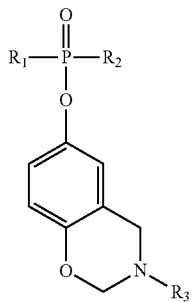

Formula 1 wherein $R_1$ and $R_2$ are each independently a C1-C20 alkyl group, a C1-C20 alkoxy group, a C6-C20 aryl group, a C6-C20 aryloxy group or a group represented by the formula below,

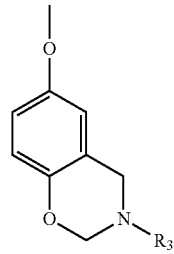

wherein $R_3$ is a hydrogen atom, a C1-C20 alkyl group, a C1-C20 alkoxy group, a C6-C20 aryl group, a C6-C20 aryloxy group, a halogenated C6-C20 aryl group, a halogenated C6-C20 aryloxy group, a C1-C20 heteroaryl group, a C1-C20 heteroaryloxy group, a halogenated C1-C20 heteroaryl group, a halogenated C1-C20 heteroaryloxy group, a C4-C20 cycloalkyl group, a halogenated C4-C20 cycloalkyl group, a C1-C20 heterocyclic group or a halogenated C1-C20 heterocyclic group.

According to another embodiment of the present invention, there is provided a polymer that is a polymerization product of a phosphorous containing benzoxazine-based monomer represented by Formula 1, above, or a polymerization product of a phosphorous containing benzoxazine-based monomer represented by Formula 1, above, and a crosslinkable compound.

According to another embodiment of the present invention, there is provided an electrode for a fuel cell comprising the polymer that is a polymerization product of a phosphorous containing benzoxazine-based monomer represented by Formula 1, above, or a polymerization product of a phosphorous containing benzoxazine-based monomer represented by Formula 1, above, and a crosslinkable compound, and a catalyst.

According to another embodiment of the present invention, there is provided an electrolyte membrane for a fuel cell comprising a crosslinked product that is a polymerization product of the phosphorous containing benzoxazine-based monomer represented by Formula 1, above, or a polymerization product of the phosphorous containing benzoxazine-based monomer represented by Formula 1, above, and a crosslinkable compound.

According to another embodiment of the present invention, there is provided a fuel cell including the electrode described above.

According to another embodiment of the present invention, there is provided a fuel cell including the electrolyte membrane described above.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
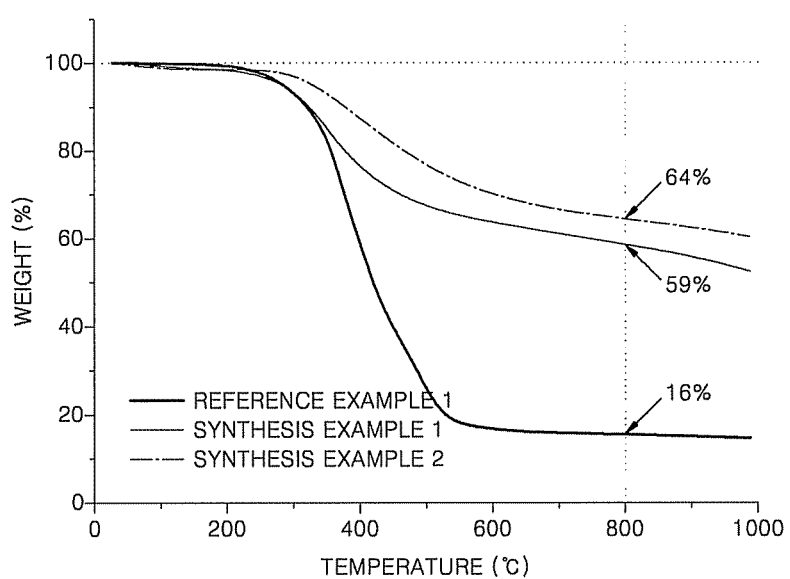
FIG. 1 shows results of thermogravimetric analyses (TGA) of tPPO-34DFA and dPPO-3AP respectively prepared according to Synthesis Examples 1 and 2 and t-BuPh-a prepared according to Reference Example 1.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

A phosphorous containing benzoxazine-based monomer according to an embodiment of the present invention is represented by Formula 1 below.

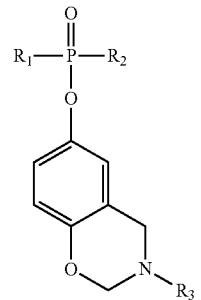

Formula 1 wherein $R_1$ and $R_2$ are each independently a C1-C20 alkyl group, a C1-C20 alkoxy group, a C6-C20 aryl group, a C6-C20 aryloxy group or a group represented by the formula below,

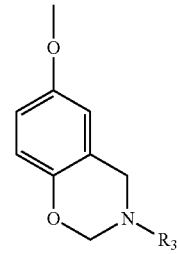

wherein $R_3$ is a hydrogen atom, a C1-C20 alkyl group, a C1-C20 alkoxy group, a C6-C20 aryl group, a C6-C20 aryloxy group, a halogenated C6-C20 aryl group, a halogenated C6-C20 aryloxy group, a C1-C20 heteroaryl group, a C1-C20 heteroaryloxy group, a halogenated C1-C20 heteroaryl group, a halogenated C1-C20 heteroaryloxy group, a C4-C20 cycloalkyl group, a halogenated C4-C20 cycloalkyl group, a C1-C20 heterocyclic group or a halogenated C1-C20 heterocyclic group.

The phosphorous containing benzoxazine-based monomer according to another embodiment of the present invention may be at least one compound selected from the group consisting of compounds represented by Formulae 2 to 4.

Formula 2

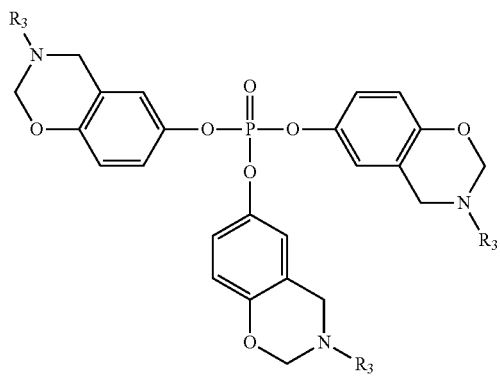

Formula 3

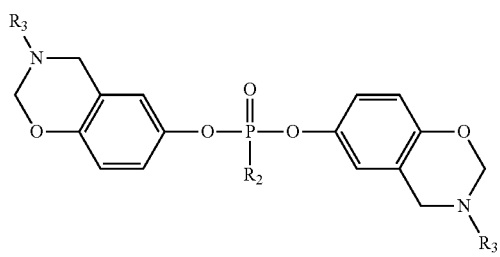

wherein $R_2$ is a C1-C10 alkyl group, a C1-C10 alkoxy group, a C6-C10 aryl group or a C6-C10 aryloxy group, and Formula 4

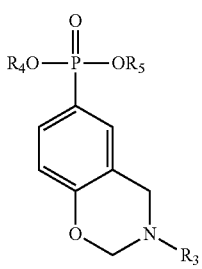

wherein $R_4$ and $R_5$ are a C6-C10 aryl group, $R_3$ of Formulae 2 to 4 is selected from the groups represented by the formulae below.

In Formulae 2 to 4, when $R_3$ is a phenyl group substituted with fluorine, since phosphorus functionality is introduced into a fluorine containing benzoxazine-based system, the phosphorous containing benzoxazine-based monomer can have excellent oxygen permeability, thermal resistance and phosphoric acid resistance, which are advantages of a fluorine containing polymer. Since the compound has a similar structure to phosphoric acid, compatibility can be increased in interfaces of gaseous state (fuel gas or oxidizing gas)—liquid state (phosphoric acid)—solid state (catalyst).

The compound of Formula 3 may be a compound represented by Formulae 5 or 6.

Formula 5

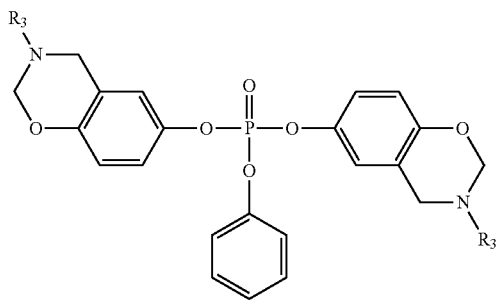

Formula 6

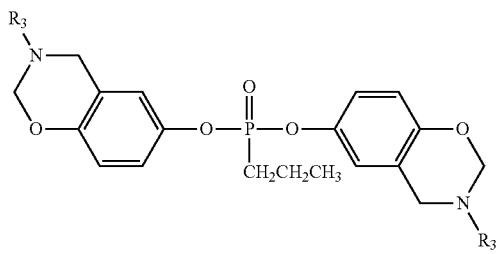

Here, $R_3$ of Formulae 5 and 6 is selected from the groups represented by the formulae below.

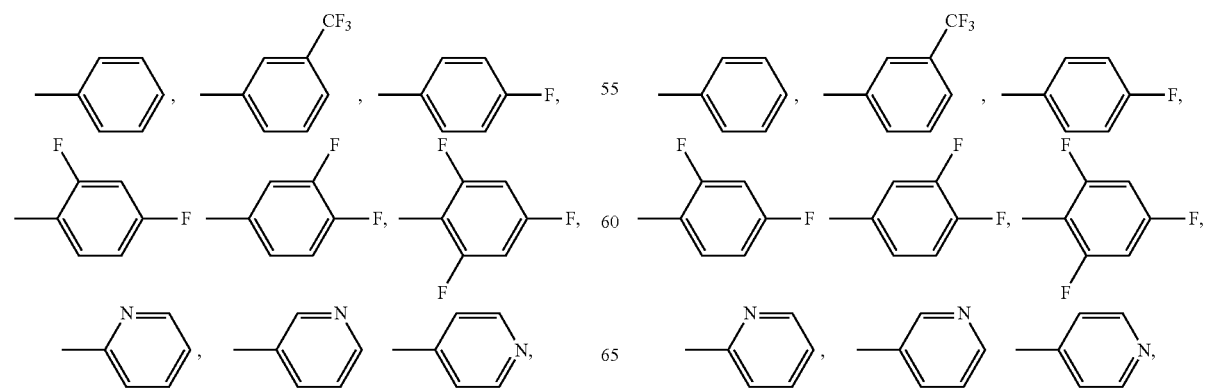

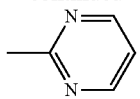

The compound represented by Formula 4 may be a compound represented by Formula 7.

Formula 7

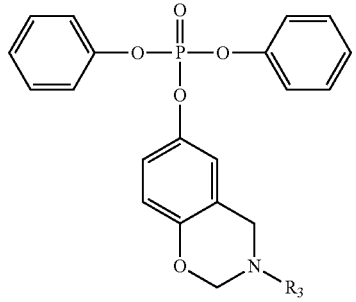

R₃ may be selected from the groups represented by the formulae below.

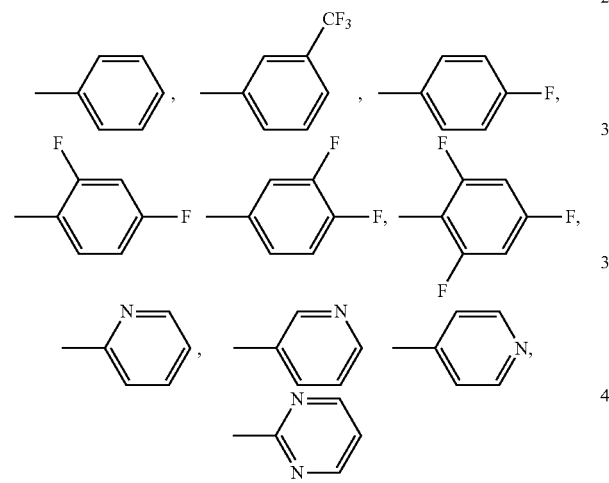

As specific, non-limiting examples, the phosphorous containing benzoxazine-based monomer may be selected from the group consisting of compounds represented by Formulae 8 to 14.

Formula 8

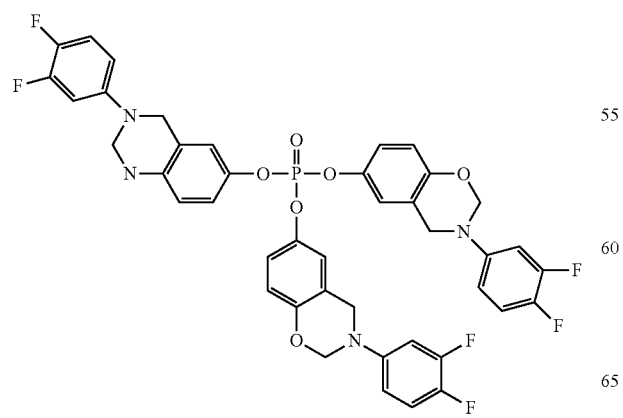

Formula 9

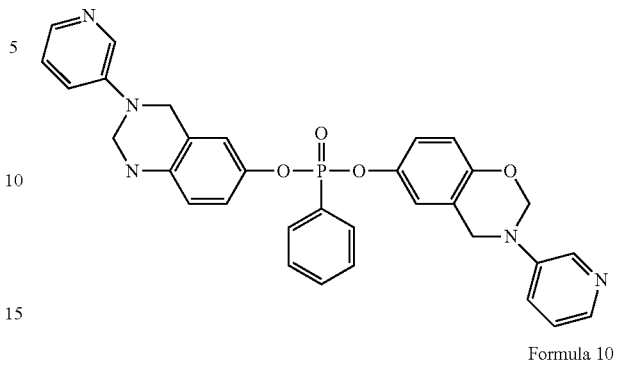

Formula 10

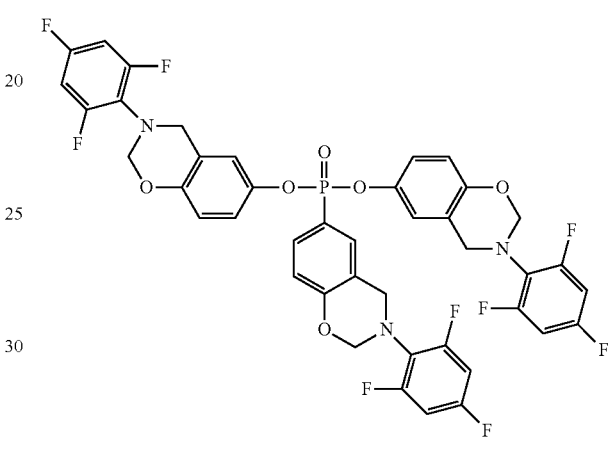

Formula 11

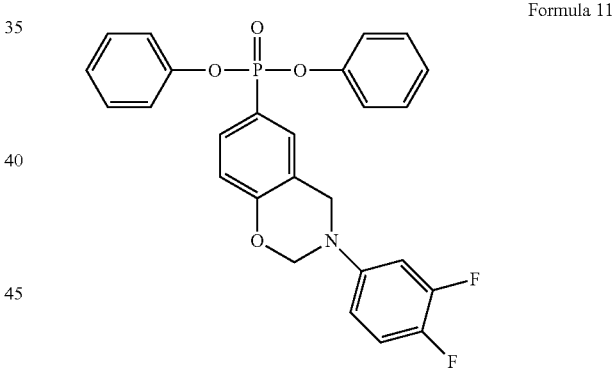

Formula 12

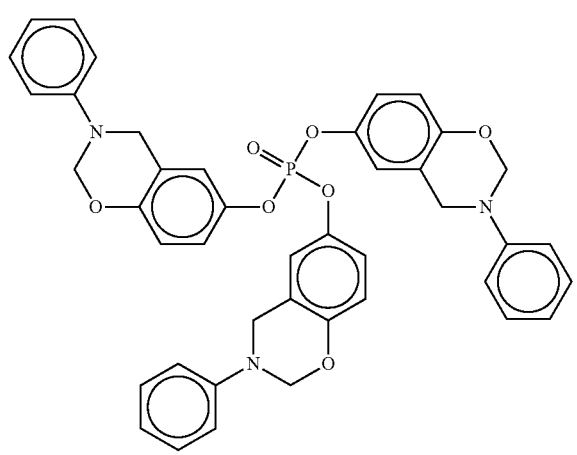

Formula 13

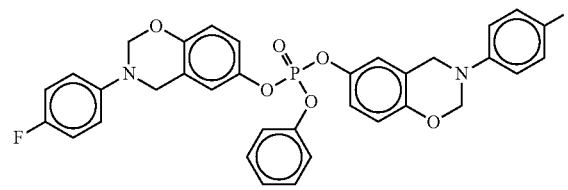

Formula 14

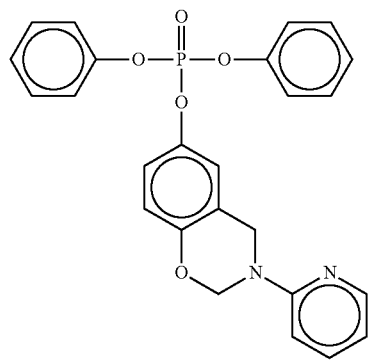

Reaction Scheme 1

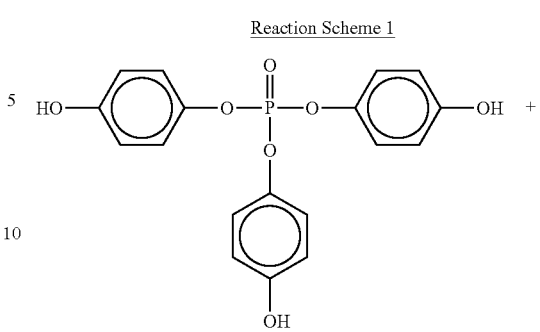

6CH$_2$O + 3 H$_2$NR$_3$ ⟶

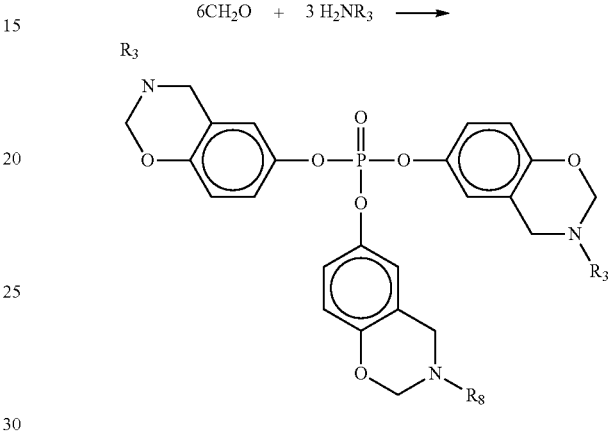

Formula 2

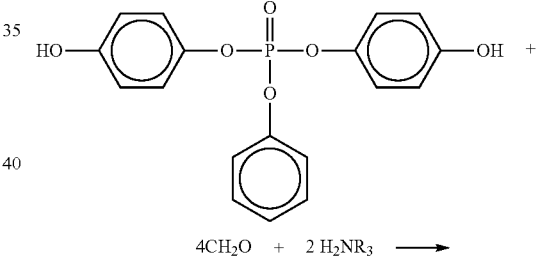

4CH$_2$O + 2 H$_2$NR$_3$ ⟶

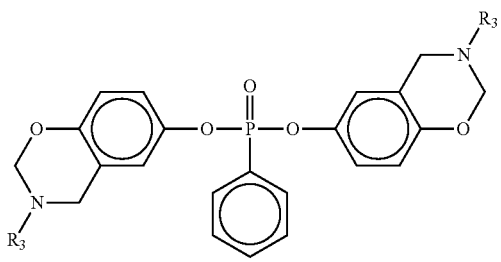

Formula 5

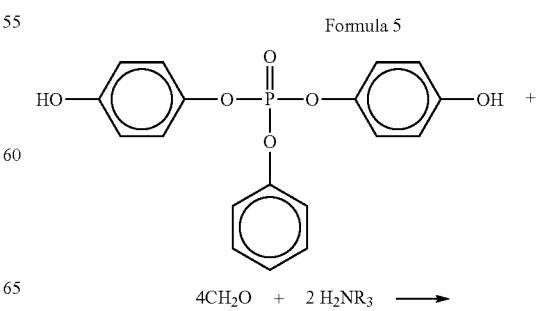

4CH$_2$O + 2 H$_2$NR$_3$ ⟶

Since the phosphorous containing benzoxazine-based monomer according to an embodiment of the present invention has excellent thermal resistance, high phosphoric acid resistance and a similar structure to phosphoric acid, and hydrophobicity of an electrode can be controlled by the monomer, compatibility can be increased in interfaces of gaseous state (fuel gas or oxidizing gas)—liquid state (phosphoric acid)—solid state (catalyst).

When the polymer prepared by polymerizing the phosphorous containing benzoxazine-based monomer is used in the formation of an electrode for a fuel cell, oxygen permeability can be improved even when air is used in a cathode, and the wettability of phosphoric acid (H$_3$PO$_4$) to the electrode and thermal stability can also be improved. Accordingly, fuel cells employing such an electrode and electrolyte membrane can operate at a high temperature with no humidity, and can have improved thermal stability and high power generation efficiency.

Hereinafter, a method of preparing a phosphorous containing benzoxazine-based monomer represented by Formula 1 according to an embodiment of the present invention will be described. For example, compounds represented by Formulae 2, 5-7 are described, but it is to be understood that other compounds can be synthesized in a similar manner.

Referring to Reaction Scheme 1 below, phosphorous containing benzoxazine-based monomers represented by Formulae 2, 5-7 can be prepared by heating a mixture of a phosphorous containing phenol-based compound, an amine compound and p-formaldehyde, with or without a solvent, refluxing the mixture, and performing a work-up process of the resultant.

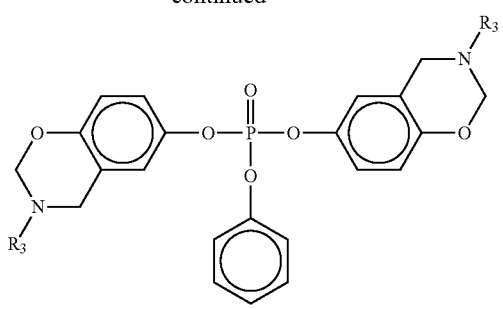

Formula 6

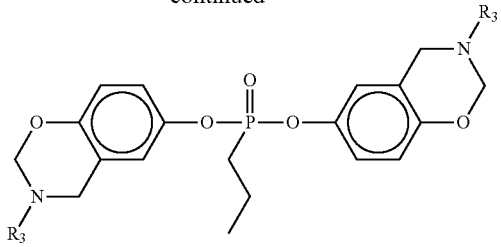

Formula 7

Here, $R_3$ of Reaction Scheme 1 is selected from the groups represented by the formulae below as defined in Formulae 2, 5-7.

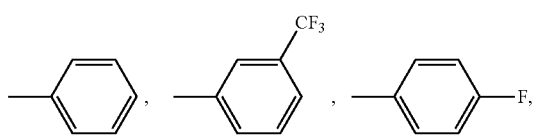

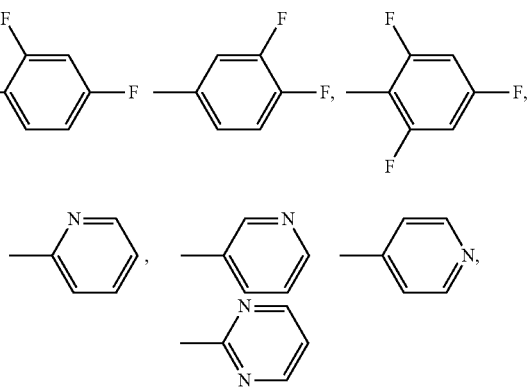

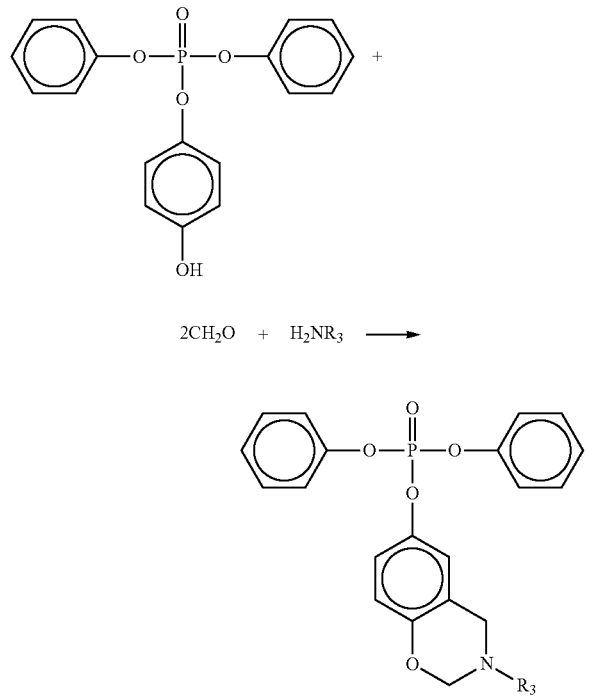

If a solvent is used, 1,4-dioxane, chloroform, dichloromethane, THF, or the like can be used as the solvent. The heating temperature may be in the range of 50 to 90° C. or more specifically, about 80° C. and can be adjusted to a temperature at which the solvent can be refluxed.

The phosphorous containing phenol-based compound used in Reaction Scheme 1 can be prepared by using 4-benzyloxyphenol and phosphoryl chloride through a protection reaction and deprotection reaction using esterification and hydrogenation as shown in Reaction Scheme 2.

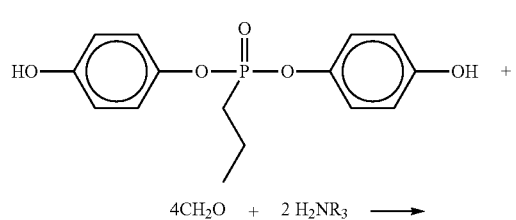

Reaction Scheme 2

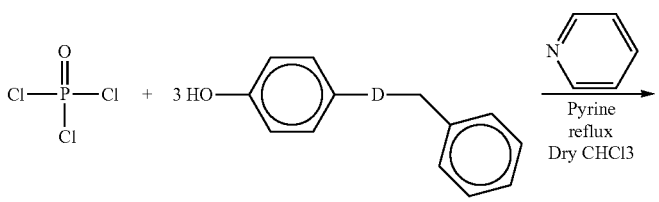

-continued
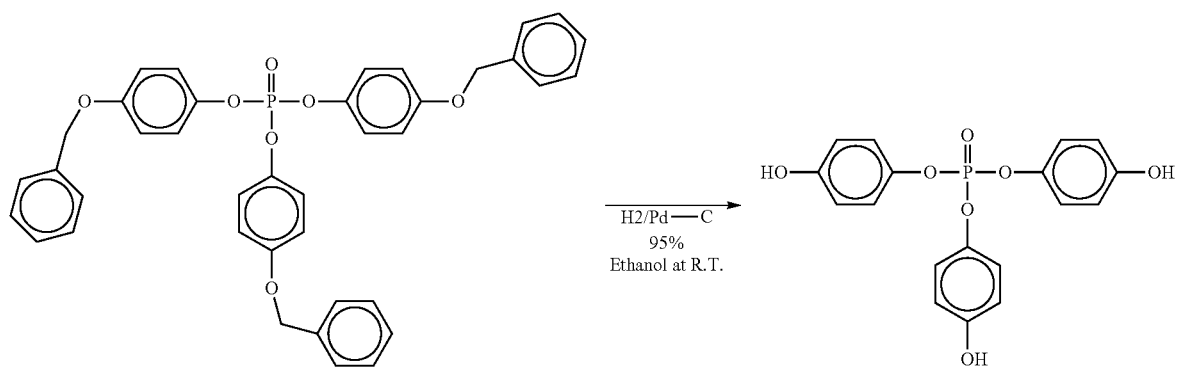
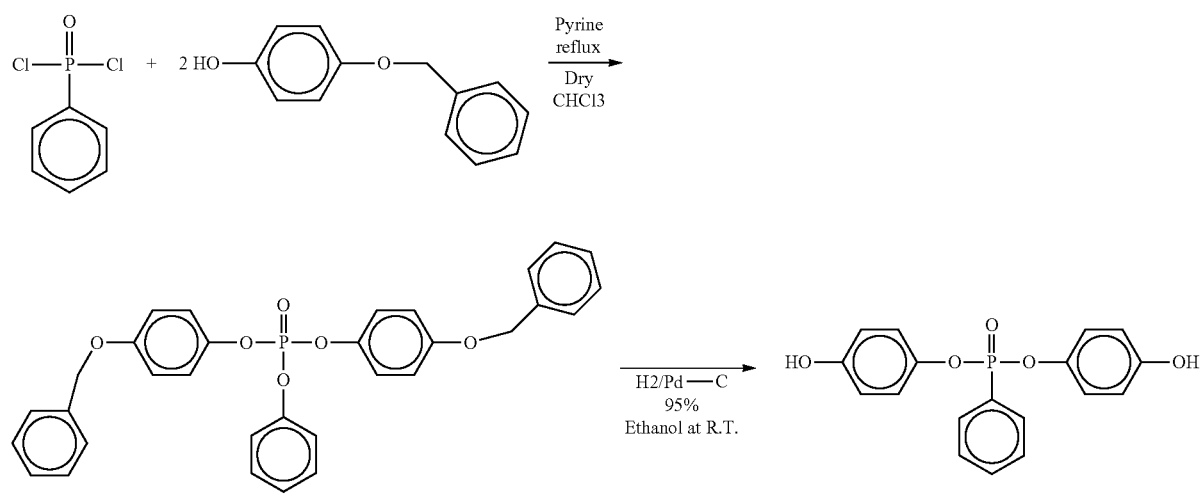
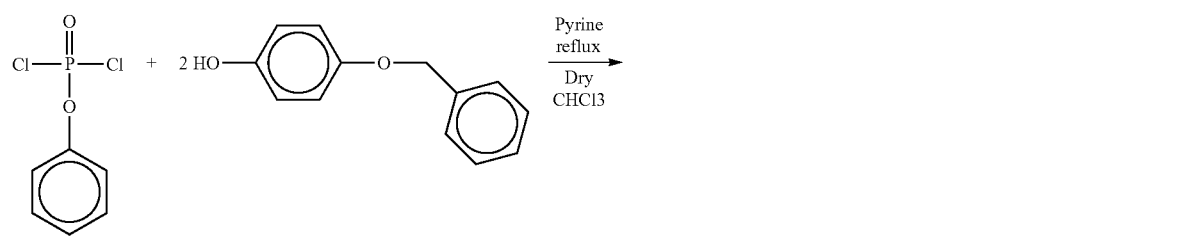
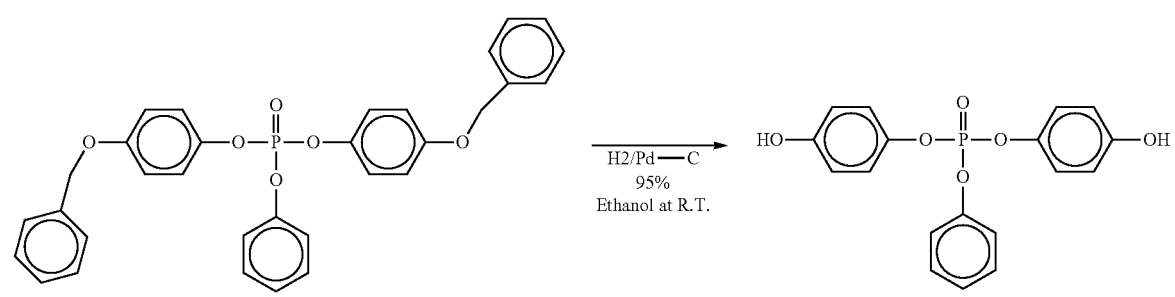
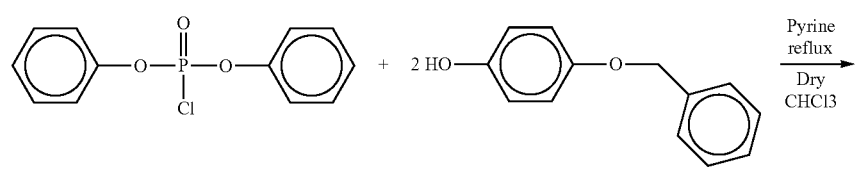

-continued

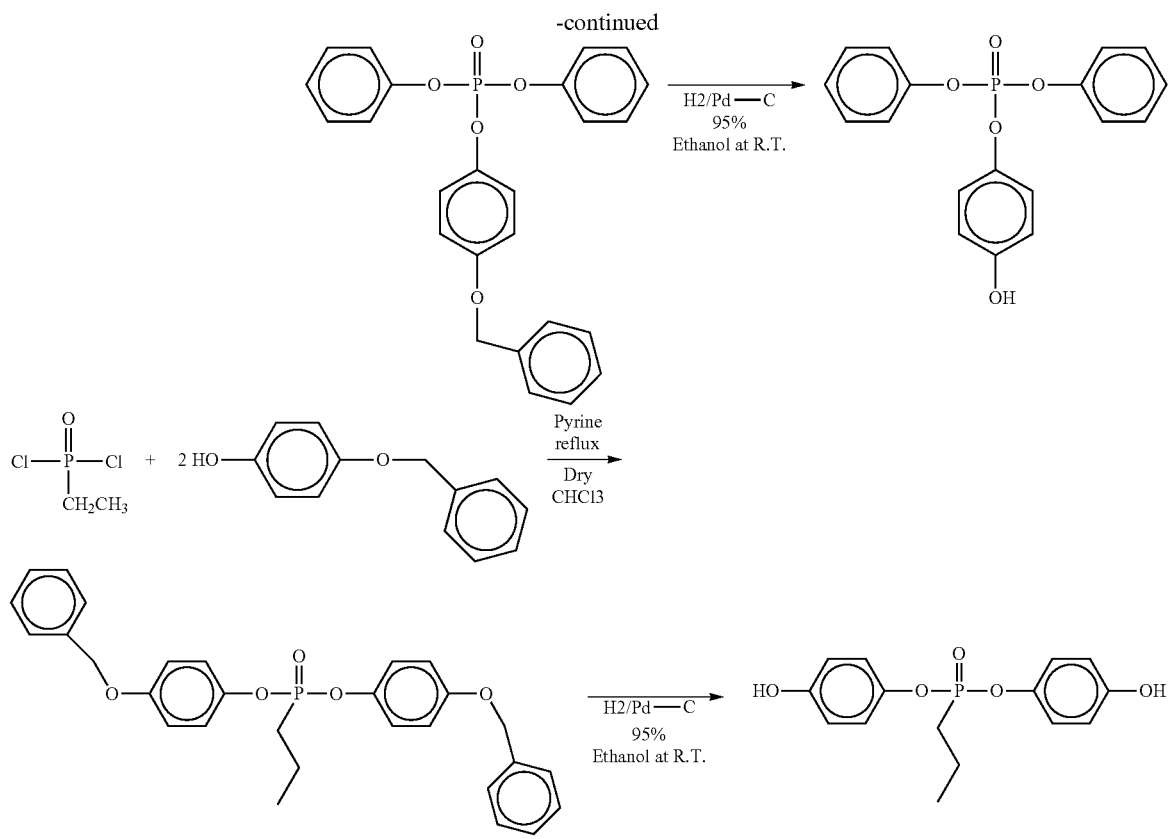

The esterification can be performed under reflux conditions in the presence of a base such as pyridine and triethylamine as shown in Reaction Scheme 1, but the esterification conditions are not limited thereto.

The hydrogenation is performed at room temperature (20-25° C.) in the presence of hydrogen and a catalyst such as Pd/C as shown in Reaction Scheme 1, but the hydrogenation conditions are not limited thereto.

According to an embodiment of the present invention there is also provided a polymer of a phosphorous containing benzoxazine-based monomer formed by polymerizing the phosphorous containing benzoxazine-based monomer represented by Formula 1.

The polymer can be prepared by dissolving the benzoxazine-based monomer in a solvent and polymerizing the solution through heat-treatment. The heat-treatment may be carried out in the range of 180 to 250° C. When the heat-treatment temperature is less than 180° C., the reactivity of the polymerization may be decreased. On the other hand, when the temperature is higher than 250° C., byproducts generated from side reactions may decrease the yields of products. A polymerization catalyst can be used, if desired.

The solvent may be N-methylpyrrolidone (NMP), dimethyl acetamide (DMAc), or the like, and the amount of the solvent may be in the range of 0.05 to 65 parts by weight based on 100 parts by weight of benzoxazine-based monomer. If the amount of the solvent is less than 0.05 parts by weight, stiffness of the membrane may not be sufficient. On the other hand, if the amount of the solvent is greater than 65 parts by weight, membrane forming properties may be decreased. In addition, aspects of the present invention also provide a polymer of phosphorous containing benzoxazine-based monomer prepared by polymerizing a phosphorous containing benzoxazine-based monomer represented by Formula 1 and a crosslinkable compound.

The crosslinkable compound may be at least one of polybenzimidazole (PBI), a polybenzimidazole-base complex, polybenzthiazole, polybenzoxazole and polyimide, but is not limited thereto.

The amount of the crosslinkable compound may be in the range of 5 to 95 parts by weight based on 100 parts by weight of the benzoxazine-based monomer represented by Formula 1.

Examples of the alkyl group are a methyl group, an ethyl group, a propyl group, an isobutyl group, a sec-butyl group, a pentyl group, an iso-amyl group, and a hexyl group. At least one of the hydrogen atoms of the alkyl group can be substituted with a halogen atom, a C1-C20 alkyl group substituted with a halogen atom (e.g.: $CCF_3$, $CHCF_2$, $CH_2F$ and $CCl_3$), a hydroxyl group, a nitro group, a cyano group, an amino group, an amidino group, a hydrazine, a hydrazone, a carboxyl group or a salt thereof, a sulfonic acid group or a salt thereof, a phosphoric acid or a salt thereof, a C1-C20 alkyl group, a C2-C20 alkenyl group, a C2-C20 alkynyl group, a C1-C20 heteroalkyl group, a C6-C20 aryl group, a C6-C20 arylalkyl group, a C6-C20 heteroaryl group or a C6-C20 heteroarylalkyl group.

Examples of the alkoxy group are a methoxy group, an ethoxy group, and a propoxy group. At least one of hydrogen atoms in the alkoxy group can be substituted with one of the functional groups described above with respect to the alkyl group.

The term "aryl group" as used herein indicates a carbocyclic aromatic system having 6-20 carbon atoms and at least one ring. The rings can be attached to each other or pendantly fused with each other. The term "aryl" includes an aromatic radical such as phenyl, naphthyl, and tetrahydronaphthyl. The aryl group may be substituted with a haloalkylene group, a nitro group, a cyano group, an alkoxy group, or a short chain alkylamino group. In addition, at least one of hydrogen atoms in the aryl group can be substituted with one of the functional groups described above with respect to the alkyl group.

The term "aryloxy group" refers to a univalent radical of the form Ar—O— where Ar is the aryl group. At least one of hydrogen atoms in the aryloxy group can be substituted with one of the functional groups described above with respect to the aryl group.

The term "heteroaryl group" used herein indicates a monovalent or bivalent, monocyclic or bicyclic aromatic organic group including 1 to 20 carbon atoms and one or more hetero atoms selected from the group consisting of nitrogen, oxygen, phosphor, and sulfur. Examples of the heteroaryl group are pyrazinyl, furanyl, thienyl, pyridyl, pyrimidinyl, isothiazolyl, oxazolyl, thiazolyl, triazolyl and 1,2,4-thiadiazolyl.

At least one of the hydrogen atoms in the heteroaryl group can be substituted with the one of the functional groups described above with respect to the alkyl group.

The term "heteroaryloxy" refers to a radical of the form heteroaryl-O—. At least one of hydrogen atoms in the heteroaryloxy group can be substituted with the one of the functional groups described above with respect to the aryl group.

The term "cycloalkyl group" as used herein indicates a non-aromatic cyclic group having 5 to 10 carbon atoms, such as, for example, a cyclohexyl group. At least one of the hydrogen atoms in the cycloalkyl group can be substituted with one of the functional groups described above with respect to the alkyl group.

The term "heterocyclic group" as used herein indicates a cyclic group including 5 to 10 carbon atoms and including one or more hetero atoms such as nitrogen, sulfur, phosphor, oxygen. At least one of the hydrogen atoms of the heterocyclic group can be substituted with one of the functional groups described above with respect to the alkyl group.

An electrode for a fuel cell according to an embodiment of the present invention includes a catalyst layer comprising a polymer of a phosphorous containing benzoxazine-based monomer that is a polymerization product of the phosphorous containing benzoxazine-based monomer represented by Formula 1 or a polymerization product of the phosphorous containing benzoxazine-based monomer and a crosslinkable compound. The catalyst layer includes a catalyst.

The polymer of the phosphorous containing benzoxazine-based monomer represented by Formula 1 is used as a binder of the electrode, and thus a conventional binder is not necessary for the electrode.

The polymer of the phosphorous containing benzoxazine-based monomer represented by Formula 1 improves the wettability of phosphoric acid, and the amount of the polymer may be in the range of 0.1 to 65 parts by weight based on 100 parts by weight of the catalyst.

When the amount of the polymer is less than 0.1 parts by weight, the wet state of the electrode is not sufficiently improved. On the other hand, when the amount of the polymer is greater than 65 parts by weight, membrane forming properties may be decreased.

As non-limiting examples, the catalyst may be Pt, a metal-Pt alloy including Pt and at least one metal selected from the group consisting of Au, Pd, Rh, Ir, Ru, Sn, Mo, Co, and Cr, or a mixture including Pt and at least one metal selected from the group consisting of Au, Pd, Rh, Ir, Ru, Sn, Mo, Co, and Cr.

Alternatively, the catalyst may be a support catalyst in which the catalyst metal is loaded on a carbonaceous support. In particular, the catalyst may be a catalyst metal including at least one of Pt, PtCo, and PtRu, in which the catalyst metal is loaded on a carbonaceous support.

The electrode may further include a binder. For example, the binder may be any binder that is commonly used in the preparation of an electrode for fuel cells.

As non-limiting examples, the binder may be at least one of poly(vinylidenefluoride), polytetrafluoroethylene, a tetrafluoroethylene-hexafluoroethylene copolymer, and perfluoroethylene. The amount of the binder may be in the range of 0.1 to 50 parts by weight based on 100 parts by weight of the catalyst. When the amount of the binder is less than 0.1 parts by weight, adhesion force of the electrode may be decreased and the catalyst layer may not be maintained. On the other hand, when the amount of the binder is greater than 50 parts by weight, electrical resistance in the electrode may be increased.

A method of preparing the electrode for a fuel cell will be described.

First, a catalyst is dispersed in a solvent to prepare a dispersion. As non-limiting examples, the solvent may be N-methylpyrrolidone (NMP), dimethylacetamide (DMAc), or the like. The amount of the solvent may be in the range of 100 to 1000 parts by weight based on 100 parts by weight of the catalyst.

A mixture of a phosphorous containing benzoxazine-based monomer represented by Formula 1 and a solvent is added to the dispersion and mixed while stirring. The mixture may further include a binder. The solvent may be N-methylpyrrolidone (NMP), dimethyl acetamide (DMAc), or the like.

An electrode is prepared by coating the mixture onto the surface of a carbon support. Here, the carbon support may be fixed on a glass substrate in order to facilitate coating. The coating can be performed using a doctor blade, a bar coating, a screen printing, or the like, but the coating method is not limited thereto.

The coated mixture may be dried at a temperature in the range of 20 to 150° C. to remove the solvent. The drying may be performed for 10 to 60 minutes, but the drying time may vary according to the drying temperature.

As described above, the electrode for a fuel cell includes a polymer of the phosphorous containing benzoxazine-based monomer represented by Formula 1 since the phosphorous containing benzoxazine-based monomer represented by Formula 1 is polymerized to form the polymer while the mixture is dried and/or while the fuel cell is operated. Meanwhile, performance of the fuel cell may be maximized by optimizing materials used to form the electrolyte membrane and/or materials used to form the electrode.

An electrolyte membrane according to an embodiment of the present invention includes a polymer of a phosphorous containing benzoxazine-based monomer that is a polymerization product of the phosphorous containing benzoxazine-based monomer represented by Formula 1 or a polymerization product of the phosphorous containing benzoxazine-based monomer and a crosslinkable compound.

The phosphorous containing benzoxazine-based monomer represented by Formula 1 has a structure including a—P=O group that can maximize hydrogen bonds within and between molecules. Thus, a polymer prepared using the phosphorous containing benzoxazine-based monomer represented by Formula 1 can have high stiffness and excellent compatibility due to having a structure similar to that of phosphoric acid.

The crosslinkable compound may be at least one of polybenzimidazole (PBI), a polybenzimidazole-base complex, polybenzthiazole, polybenzoxazole and polyimide, but is not limited thereto. The polybenzimidazole-base complex is disclosed in Korean Patent Application No. 2007-102579 filed by the inventors of the present invention.

According to an embodiment of the present invention, if the crosslinkable compound is polybenzimidazole (PBI) or a polybenzimidazole-base complex, the electrolyte membrane may be a crosslinked product of a polybenzoxazine-based compound which is prepared by curing a mixture of a thermosetting resin of polybenzoxazine and a thermoplastic resin of polybenzimidazole or a mixture of a thermosetting resin of polybenzoxazine and a thermoplastic resin of a polybenzimidazole-base complex.

Since the electrolyte membrane according to an embodiment of the present invention is prepared as a crosslinked product of a polybenzoxazine-based compound having high thermal resistance, the electrolyte membrane has high mechanical and chemical stability and excellent durability at a high operating temperature, and thus has a long lifetime.

Hereinafter, a method of preparing the electrolyte membrane according to an embodiment of the present invention will be described. An electrolyte membrane formed using a crosslinkable compound is described herein. However, when an electrolyte membrane is prepared only using the phosphorous containing benzoxazine-based monomer represented by Formula 1, the preparation process is the same as those described herein, except that the crosslinkable compound is not used.

First, a phosphorus-containing benzoxazine-based monomer represented by Formula 1 is blended with a crosslinkable compound, as described above, and the mixture is cured at a temperature in the range of 50 to 250° C., or more particularly, in a range of 80 to 220° C. The cured mixture is impregnated with a proton conductor such as an acid to prepare an electrolyte membrane.

The amount of the crosslinkable compound may be in the range of 5 to 95 parts by weight based on 100 parts by weight of the benzoxazine-based monomer of Formula 1. When the amount of the crosslinkable compound is less than 5 parts by weight, the proton conductivity may be decreased since phosphoric acid may not be impregnated. On the other hand, when the amount of the crosslinkable compound is greater than 95 parts by weight, gas may permeate since the crosslinked polybenzoxazines melt in a polyphosphoric acid in the presence of an excessive amount of phosphoric acid.

An electrolyte membrane is formed using a mixture of the first benzoxazine-based monomer represented by Formula 1 and a crosslinkable compound.

The membrane can be formed using a tape casting method, or a conventionally used coating method. An example of the coating method can be a method of casting the mixture on a support using a doctor blade. For example, the doctor blade having a 250-500 µm gap may be used. In forming the membrane using the doctor blade method, the method may further include removing the support by exfoliating the electrolyte membrane from the support after the curing and before the impregnation. In order to remove the support, the resultant may be immersed in distilled water at a temperature in the range of 60 to 80° C.

The support may be any material that can support the electrolyte membrane, such as, for example, a glass substrate, polyimide film, and the like. The above-described actions to remove the support are not necessary in the tape casting method, since the tape cast membrane is easily separated from a support material such as polyethylene terephthalate used in tape casting and placed in an oven for curing.

In addition, when the membrane is formed using a mixture of benzoxazine-based monomer and polybenzimidazole through a tape casting method, filtering the mixture may further be included in the method.

The prepared membrane is cured through heat treatment, and impregnated with a proton conductor such as an acid to form an electrolyte membrane.

The proton conductor may be a phosphoric acid, a C1-C20 organic phosphonic acid, or the like, but is not limited thereto. The C1-C20 organic phosphonic acid may be ethyl phosphonic acid, methyl phosphonic acid, etc.

The amount of the proton conductor may be 300 to 1000 parts by weight based on 100 parts by weight of the electrolyte membrane. For example, 85% by weight of an aqueous phosphoric acid solution may be used at 80° C. for 2.5 to 14 hours to impregnate the electrolyte membrane, but the concentration of the acid is not limited.

A method of preparing a fuel cell using the electrode according to an embodiment of the present invention will be described.

Any electrolyte membrane that is commonly used in the preparation of fuel cells can be used herein. Alternatively, an electrolyte membrane including a polymer of a phosphorous containing benzoxazine-based monomer which is a polymerization product of a phosphorous containing benzoxazine-based monomer represented by Formula 1 and a crosslinkable compound, that is, a crosslinked product of a polybenzoxazine-based compound as described above may be used.

In particular, performance of the fuel cell may be maximized by using the electrolyte membrane including the crosslinked product of the polybenzoxazine-based compound.

The electrolyte membrane that is commonly used in the preparation of fuel cells may be a polybenzimidazole electrolyte membrane, a polybenzoxazine-polybenzimidazole copolymer electrolyte membrane, a PTFE porous membrane, or the like.

A membrane and electrode assembly for fuel cells according to an embodiment of the present invention will be described. Here, the "membrane and electrode assembly (MEA)" indicates a structure in which electrodes each composed of a catalyst layer and a diffusion layer are laminated on respective sides of an electrolyte membrane.

The MEA according to aspects of the present invention may be prepared by placing electrodes including the catalyst layer on respective sides of the obtained electrolyte membrane and assembling the electrodes and electrolyte membrane at a high temperature under a high pressure, and then applying a fuel diffusion layer.

The assembling may be performed at a temperature at which the electrolyte membrane softens and at a pressure under 0.1 to 3 ton/cm², and preferably under about 1 ton/cm².

Then, a bipolar plate is respectively installed into each electrode-membrane assembly to complete a fuel cell. The bipolar plate has a fuel supply groove and a current collecting property.

The fuel cell may be a polymer electrolyte membrane fuel cell (PEMFC), but the fuel cell is not limited thereto.

According to an embodiment of the present invention, the polymer of the phosphorous containing benzoxazine-based monomer may be used for the preparation of an electrode and an electrolyte membrane for a fuel cell. Power generation performance of a fuel cell employing the electrode and the electrolyte membrane can be significantly improved.

Hereinafter, aspects of the present invention will be described in greater detail with reference to the following examples. The following examples are for illustrative purposes only and are not intended to limit the scope of the invention.

SYNTHESIS EXAMPLE 1

Preparation of tPPO-34DFA represented by Formula 8

3.0 g (0.008 mol) of tris(4-hydroxyphenyl) phosphate, 1.68 g (0.053 mol) of p-formaldehyde and 3.41 g (0.026 mol) of 3,4-difluoroaniline were added to a 100 ml one-neck round-bottom flask and mixed in an oil bath at 90° C. When the initially opaque mixture became a dark brown transparent gel type material after about 30 minutes, the reaction was quenched using tetrahydrofuran (THF), and then the mixture was cooled to room temperature. The cooled crude product was base-washed twice through a solvent extraction using a 1N NaOH aqueous solution, and washed once with deionized water. After washing, the organic layer was dried with $MgSO_4$ and filtered. The residual solution was dried using a rotary evaporator to remove the solvent, and the purified product was dried in a vacuum oven at 40° C. for 6 hours to obtain tPPO-34DFA represented by Formula 8.

Figure 4:
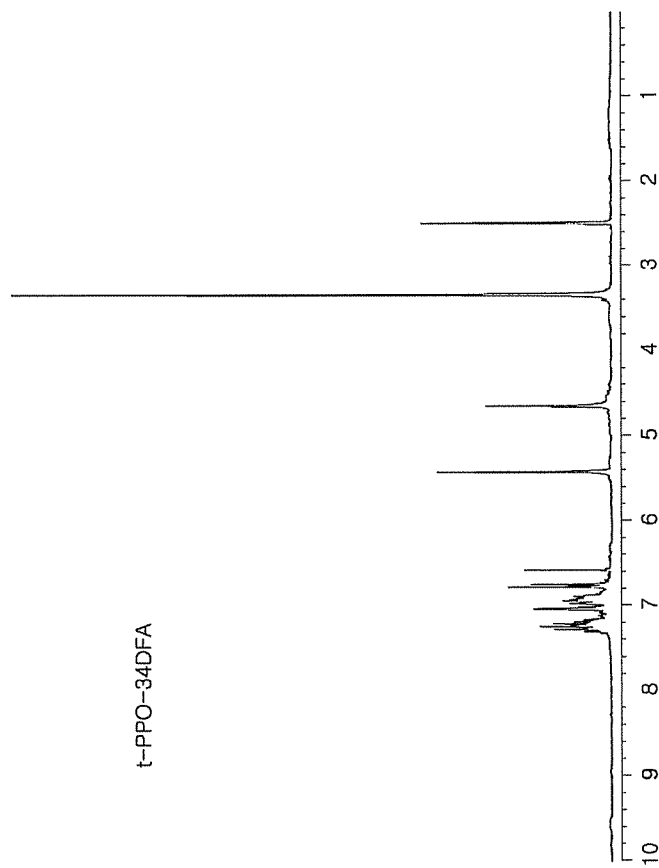
FIG. 4 shows a nuclear magnetic resonance (NMR) spectrum of tPPO-34DFA prepared according to Synthesis Example 1.

The structure of tPPO-34DFA was identified by a nuclear magnetic resonance (NMR) spectrum as shown in FIG. 4.

SYNTHESIS EXAMPLE 2

Preparation of dPPO-3AP Represented by Formula 9

Figure 5:
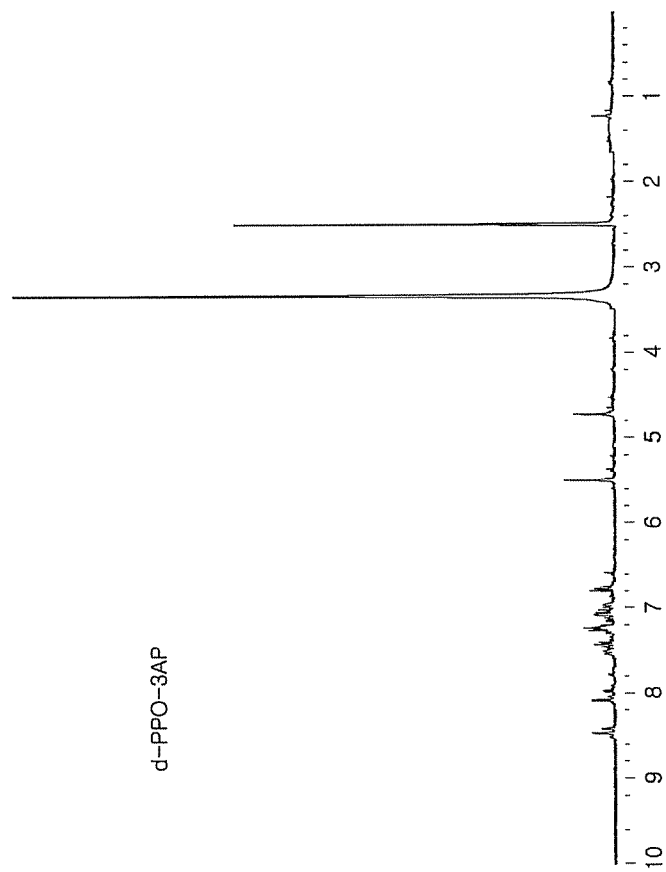
FIG. 5 shows a NMR spectrum of dPPO-3AP represented by Formula 10 prepared according to Synthesis Example 2.

10.0 g (0.028 mol) of bis(4-hydroxyphenyl)phenyl phosphate, 3.88 g (0.123 mol) of p-formaldehyde and 5.78 g (0.061 mol) of 3-aminopyridine were added to a 100 ml one-neck round-bottom flask and mixed in an oil bath at 90° C. When the initially opaque mixture became a dark brown transparent gel type material after about 30 minutes, the reaction was quenched using tetrahydrofuran (THF), and then the mixture was cooled to room temperature. The cooled crude product was base-washed twice through a solvent extraction using a 1N NaOH aqueous solution, and washed once with deionized water. After washing, the organic layer was dried with $MgSO_4$ and filtered. The residual solution was dried using a rotary evaporator to remove the solvent, and the purified product was dried in a vacuum oven at 40° C. for 6 hours to obtain dPPO-3AP represented by Formula 9. The structure of dPPO-3AP was identified by a nuclear magnetic resonance (NMR) spectrum as shown in FIG. 5.

SYNTHESIS EXAMPLE 3

Preparation of tPPO-246TFA Represented by Formula 10

1.5 g (0.004 mol) of tris(4-hydroxyphenyl) phosphate, 0.84 g (0.0265 mol) of p-formaldehyde and 1.94 g (0.013 mol) of 2,4,6-trifluoroaniline were added to a 100 ml one-neck round-bottom flask and mixed in an oil bath at 90° C. When the initially opaque mixture became a dark brown transparent gel type material after about 30 minutes, the reaction was quenched using tetrahydrofuran (THF), and then the mixture was cooled to room temperature. The cooled crude product was base-washed twice through a solvent extraction using a 1N NaOH aqueous solution, and washed once with deionized water. After washing, the organic layer was dried with $MgSO_4$ and filtered. The residual solution was dried using a rotary evaporator to remove the solvent, and the purified product was dried in a vacuum oven at 40° C. for 6 hours to obtain tPPO-246TFA represented by Formula 10.

SYNTHESIS EXAMPLE 4

Preparation of m-PPO-34DFA Represented by Formula 11

1.5 g (0.004 mol) of 4-hydroxyphenyl diphenyl phosphate, 0.305 g (0.01 mol) of p-formaldehyde and 0.62 g (0.005 mol) of 3,4-difluoroaniline were added to a 100 ml one-neck round-bottom flask and mixed in an oil bath at 90° C. When the initially opaque mixture became a dark brown transparent gel type material after about 30 minutes, the reaction was quenched using tetrahydrofuran (THF), and then the mixture was cooled to room temperature. The cooled crude product was base-washed twice through a solvent extraction using a 1N NaOH aqueous solution, and washed once with deionized water. After washing, the organic layer was dried with $MgSO_4$ and filtered. The residual solution was dried using a rotary evaporator to remove the solvent, and the purified product was dried in a vacuum oven at 40° C. for 6 hours to obtain m-PPO-34DFA represented by Formula 11.

SYNTHESIS EXAMPLE 5

Preparation of t-PPO-a Represented by Formula 12

10 g (0.027 mol) of tris(4-hydroxyphenyl) phosphate, 5.56 g (0.176 mol) of p-formaldehyde and 8.2 g (0.088 mol) of aniline were added to a 250 ml one-neck round-bottom flask and mixed in an oil bath at 90° C. When the initially opaque mixture became a dark brown transparent gel type material after about 30 minutes, the reaction was quenched using tetrahydrofuran (THF), and then the mixture was cooled to room temperature. The cooled crude product was base-washed twice through a solvent extraction using a 1N NaOH aqueous solution, and washed once with deionized water. After washing, the organic layer was dried with $MgSO_4$ and filtered. The residual solution was dried using a rotary evaporator to remove the solvent, and the purified product was dried in a vacuum oven at 40° C. for 6 hours to obtain t-PPO-a represented by Formula 12.

SYNTHESIS EXAMPLE 6

Preparation of d-PPO-4FA Represented by Formula 13

5 g (0.014 mol) of bis(4-hydroxyphenyl)phenyl phosphate, 1.94 g (0.061 mol) of p-formaldehyde and 3.45 g (0.031 mol) of 3-fluoroaniline were added to a 100 ml one-neck round-bottom flask and mixed in an oil bath at 90° C. When the initially opaque mixture became a dark brown transparent gel type material after about 30 minutes, the reaction was quenched using tetrahydrofuran (THF), and then the mixture was cooled to room temperature. The cooled crude product was base-washed twice through a solvent extraction using a 1N NaOH aqueous solution, and washed once with deionized water. After washing, the organic layer was dried with $MgSO_4$ and filtered. The residual solution was dried using a rotary evaporator to remove the solvent, and the purified product was dried in a vacuum oven at 40° C. for 6 hours to obtain dPPO-4FA represented by Formula 13.

SYNTHESIS EXAMPLE 7

Preparation of m-PPO-2AP Represented by Formula 14

5 g (0.0146 mol) of 4-hydroxyphenyl diphenyl phosphate, 1.012 g (0.032 mol) of p-formaldehyde and 1.515 g (0.016 mol) of 2-aminopyridine were added to a 100 ml one-neck round-bottom flask and mixed in an oil bath at 90° C. When the initially opaque mixture became a dark brown transparent gel type material after about 30 minutes, the reaction was quenched using tetrahydrofuran (THF), and then the mixture was cooled to room temperature. The cooled crude product was base-washed twice through a solvent extraction using a 1N NaOH aqueous solution, and washed once with deionized water. After washing, the organic layer was dried with $MgSO_4$ and filtered. The residual solution was dried using a rotary evaporator to remove the solvent, and the purified product was dried in a vacuum oven at 40° C. for 6 hours to obtain m-PPO-2AP represented by Formula 14.

SYNTHESIS EXAMPLE 8

Figure 17:
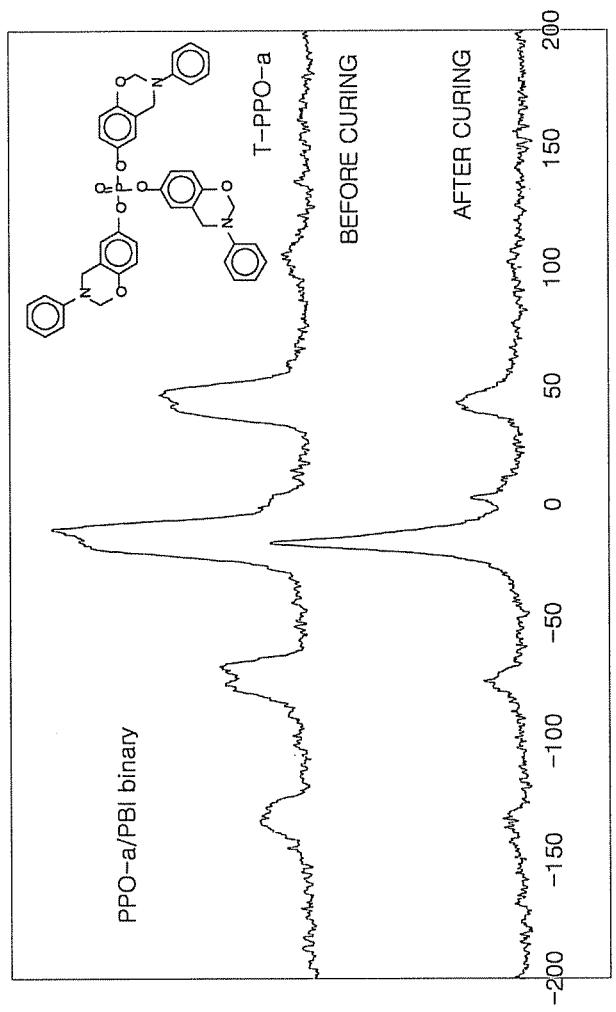
FIG. 17 is a graph illustrating a solid nuclear magnetic resonance (NMR) spectrum of a polymer of t-PPO-a represented by Formula 12 and PBI.

Preparation of a polymer of t-PPO-a Represented by Formula 12 and Polybenzimidazole 20 g of t-PPO-a represented by Formula 12, 10.8 g of polybenzimidazole, and dimethyl acetamide (DMAc) were blended, and the mixture was cured at about 220° C. to obtain a polymer of t-PPO-a represented by Formula 12 and polybenzimidazole. The structure of the solid-phase polymer of t-PPO-a represented by Formula 12 and polybenzimidazole was identified by a solid nuclear magnetic resonance (NMR) spectrum, and the results are shown in FIG. 17. The NMR was performed using a Varian Unity INOVA600 at 600 MHz.

SYNTHESIS EXAMPLE 9

Preparation of a polymer m-PPO-2A represented by Formula 14 and Polybenzimidazole A polymer of m-PPO-2A represented by Formula 14 and polybenzimidazole was prepared in the same manner as in Synthesis Example 8, except that m-PPO-2A represented by Formula 14 was used instead of t-PPO-a represented by Formula 12.

REFERENCE EXAMPLE 1

Preparation of t-BuPh-a 15 g (0.1 mol) of t-butylphenol, 6.31 g (0.21 mol) of p-formaldehyde and 10.24 g (0.11 mol) of aniline were added to a 100 ml one-neck round-bottom flask and mixed in an oil bath at 90° C. When the initially opaque mixture became a dark brown transparent gel type material after about 30 minutes, the reaction was quenched using tetrahydrofuran (THF), and then the mixture was cooled to room temperature. The cooled crude product was base-washed twice through a solvent extraction using a 1N NaOH aqueous solution, and washed once with deionized water. After washing, the organic layer was dried with $MgSO_4$ and filtered. The residual solution was dried using a rotary evaporator to remove the solvent, and the purified product was dried in a vacuum oven at 40° C. for 6 hours to obtain t-BuPh-a.

Figure 6:
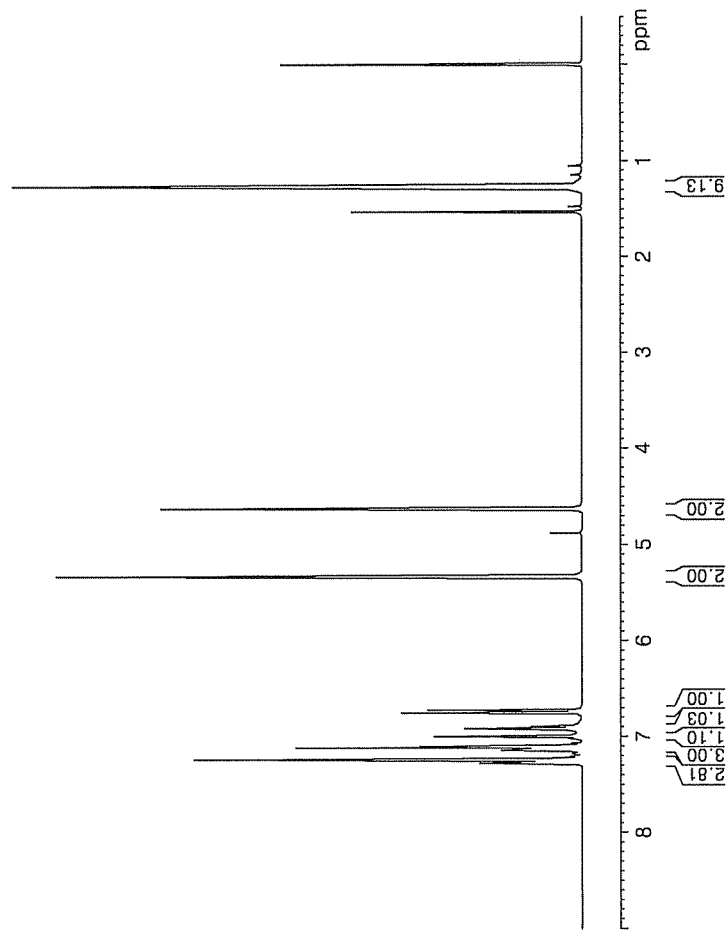
FIG. 6 shows a NMR spectrum of t-BuPh-a prepared according to Reference Example 1.

The structure of t-BuPh-a was identified by a nuclear magnetic resonance (NMR) spectrum as shown in FIG. 6.

Thermal stability of tPPO-34DFA and dPPO-3AP respectively prepared according to Synthesis Examples 1 and 2 and t-BuPh-a prepared according to Reference Example 1 was measured by performing thermogravimetric analysis (TGA), and the results are shown in FIG. 1. Thermal weight loss was measured at 800° C. in FIG. 1. Referring to FIG. 1, the thermal stability of tPPO-34DFA and dPPO-3AP was greater than that of t-BuPh-a.

EXAMPLE 1

Preparation of an Electrode for a Fuel Cell and a Fuel Cell Using the Electrode

To prepare the cathode, 1 g of a catalyst in which 50% by weight of PtCo was loaded on carbon and 3 g of NMP as a solvent were added to a container, and the mixture was agitated using a mortar to prepare a slurry. A solution of 10% by weight of tPPO-34DFA represented by Formula 8 prepared according to Synthesis Example 3 and NMP was added to the slurry and agitated to provide 0.025 g of the compound represented by Formula 8. Then, a solution of 5% by weight of polyvinylidenefluoride and NMP was added to the mixture to set the amount of the polyvinylidenefluoride to 0.025 g, and the mixture was mixed for 10 minutes to prepare a slurry for a cathode catalyst layer.

Carbon paper was cut into pieces of 4×7 $cm^2$ in size, and the pieces were fixed on a glass plate and coated with the slurry using a doctor blade (Sheen instrument), wherein the gap interval of the doctor blade was 600 μm.

The slurry for a cathode catalyst layer was coated onto the carbon paper and dried at room temperature for 1 hour, at 80° C. for 1 hour, at 120° C. for 30 minutes and at 150° C. for 15 minutes to prepare a cathode (a fuel electrode). The loading amount of Pt/Co in the prepared cathode was 3.0 mg/$cm^2$.

To prepare the anode, 2 g of a catalyst in which 50% by weight of Pt was loaded on carbon and 9 g of NMP solvent were added to a container and the mixture was agitated in a high-speed agitator for 2 minutes. Then, a solution of 0.05 g of polyvinylidenefluoride dissolved in 1 g of NMP was added thereto and agitated for 2 minutes to prepare a slurry for an anode catalyst layer. The slurry was coated using a bar coater onto carbon paper onto which a microporous layer had been previously coated. The loading amount of Pt in the prepared anode was 1.4 mg/$cm^2$.

To prepare the electrolyte membrane, 60 parts by weight of benzoxazine-based monomer A represented by the formula below, 3 parts by weight of benzoxazine-based monomer B, represented by the formula below, and 37 parts by weight of polybenzimidazole were blended, and the mixture was cured at about 220° C.

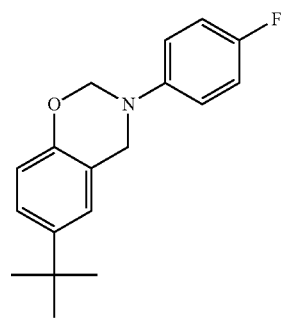

benzoxazine-based monomer A

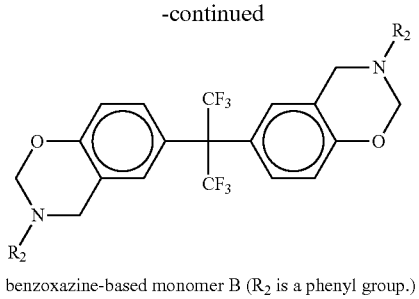

benzoxazine-based monomer B ($R_2$ is a phenyl group.)

Then, the resultant was impregnated with 85% by weight of phosphoric acid at 80° C. for longer than 4 hours to prepare the electrolyte membrane. The amount of phosphoric acid was about 480 parts by weight based on 100 parts by weight of the electrolyte membrane.

The loading amount of Pt/Co in the prepared cathode was about 2.33 mg/cm$^2$, and the loading amount of Pt in the prepared anode was 1.4 mg/cm$^2$.

A membrane electrode assembly (MEA) was prepared by interposing the electrolyte membrane between the cathode and the anode. The cathode and anode were not impregnated with phosphoric acid.

A 200 μm TEFLON membrane for a main gasket and a 20 μm TEFLON membrane for a sub gasket were overlapped on an interface between the electrodes and electrolyte membrane in order to prevent gas permeation between the cathode and the anode. The pressure applied to the MEA was adjusted to 1, 2, 3 N-m torque step by step using a wrench to assemble a cell.

Characteristics of the fuel cell were measured while operating the fuel cell by supplying hydrogen to the anode at 100 ccm and supplying air to the cathode at 252 ccm at 150° C. The electrolyte membrane was not hydrated. Since cell efficiency increases with time when an electrolyte doped with phosphoric acid is used, the final efficiency was measured after aging was performed until the operational voltage was maximized. The area of the cathode and the anode was fixed to 7.84 cm$^2$ (2.8×2.8), the thickness of the cathode was about 430 μm and the thickness of the anode was about 390 μm, although the thicknesses of the cathode and the anode varied according to the distribution of the carbon paper.

EXAMPLE 2

Preparation of an Electrode for a Fuel Cell and a Fuel Cell Using the Electrode

A cathode and a fuel cell using the cathode were prepared in the same manner as in Example 1, except that dPPO-3AP represented by Formula 9 was used instead of tPPO-3A4DFA represented by Formula 8 in the preparation of the cathode.

EXAMPLE 3

Preparation of an Electrode for a Fuel Cell and a Fuel Cell Using the Electrode

A cathode and a fuel cell using the cathode were prepared in the same manner as in Example 1, except that tPPO-246TFA represented by Formula 10 was used instead of tPPO-3A4DFA represented by Formula 8 in the preparation of the cathode.

EXAMPLE 4

Preparation of an Electrode for a Fuel Cell and a Fuel Cell Using the Electrode

A cathode and a fuel cell using the cathode were prepared in the same manner as in Example 1, except that m-PPO-34DFA represented by Formula 11 was used instead of tPPO-3A4DFA represented by Formula 8 in the preparation of the cathode.

COMPARATIVE EXAMPLE 1

Preparation of an Electrode for a Fuel Cell and a Fuel Cell Using the Electrode

A cathode and a fuel cell using the cathode were prepared in the same manner as in Example 1, except that tPPO-3A4DFA represented by Formula 8 was not added in the preparation of the cathode.

Figure 2:
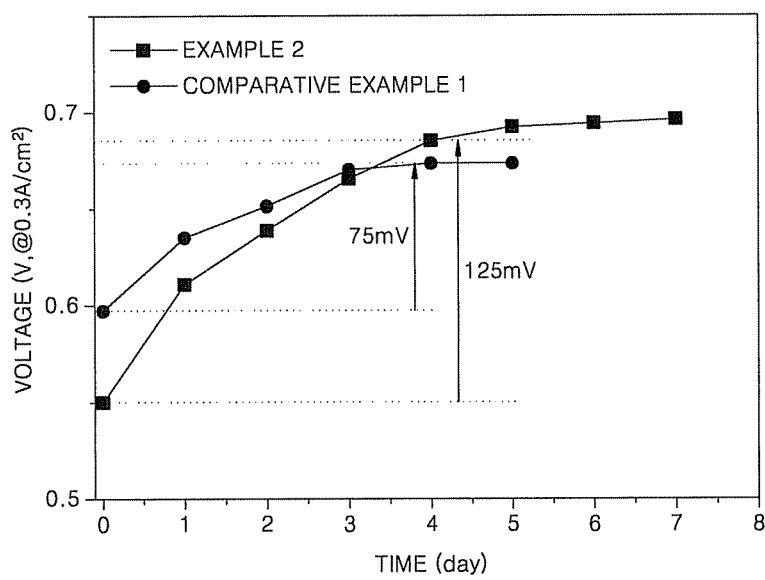
FIG. 2 shows voltage changes with time in fuel cells prepared according to Example 2 and Comparative Example 1.

Voltage changes with time in fuel cells prepared according to Example 2 and Comparative Example 1 were measured to evaluate cell performance, and the results are shown in FIG. 2. Referring to FIG. 2, the performance of the fuel cell according to Example 2 was greater than that of the fuel cell according to Comparative Example 1.

Figure 3:
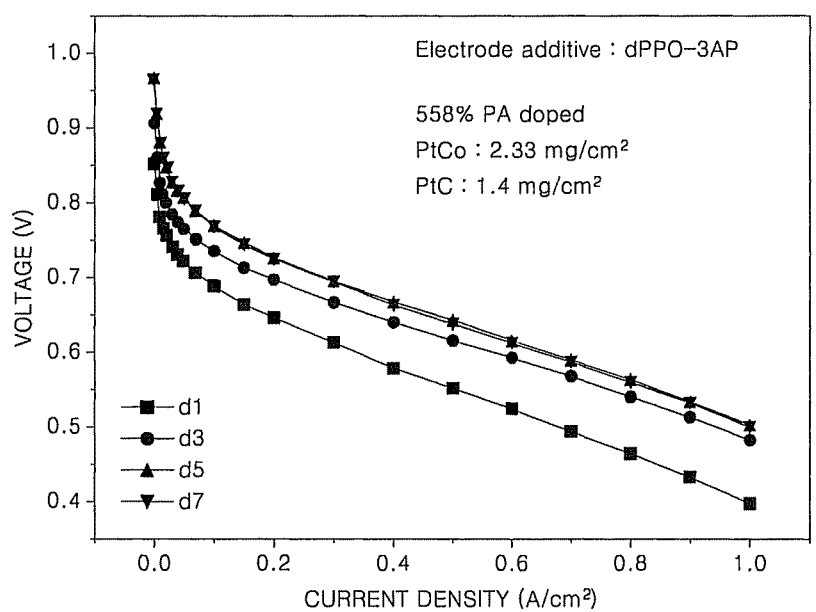
FIG. 3 shows cell potential changes according to current density in a fuel cell prepared according to Example 2.

In addition, cell voltage characteristics with respect to current density were measured in a fuel cell prepared according to Example 2, and the results are shown in FIG. 3. The d1, d3, d5 and d7 of FIG. 3 respectively indicate first day, third day, fifth day and seventh day. Referring to FIG. 3, activation was quickly increased until the third day and was completed on the fifth day. Thus, it can be seen that the high performance of fuel cells can be maintained with the passage of time.

Performance of fuel cells prepared according to Examples 1 to 4 and Comparative Example 1 was tested and the results are shown in Table 1.

TABLE 1

|  | Voltage at 0.3 A/cm$^2$ (V) | Mass transfer overpotential η at 0.3 A/cm$^2$ (mV) | Exchange current density (A/cm$^2$) | Pt availability (%) |
|---|---|---|---|---|
| d-PPO-3AP (Example 2) | 0.697 | 12 | $4.2 \times 10^{-5}$ | 19 |
| tPPO34DFA (Example 1) | 0.692 | 16 | $7.1 \times 10^{-5}$ | 17.8 |
| tPPO246TFA (Example 3) | 0.689 | 18 | $7.1 \times 10^{-5}$ | N/A |
| m-PPO-34DFA (Example 4) | 0.683 | 16 | $6.9 \times 10^{-5}$ | 16.4 |
| Comparative Example 1 | 0.678-0.692 | 20-22 | $3.8 \times 10^{-5} \sim 4.1 \times 10^{-5}$ | 17.7 |

Referring to Table 1, fuel cells of Examples 1 to 4 have lower mass transfer overpotential and higher exchange current density compared to the fuel cell of Comparative Example 1

Thus, the oxygen permeability of fuel cells of Examples 1 to 4 is higher than that of Comparative Example 1. Typically, as oxygen permeability increases, mass transfer overpotential decreases and exchange current density increases.

In addition, according to Table 1, Pt availability of fuel cells of Examples 1 to 4 is higher than that of Comparative Example 1. This indicates that the amount of phosphoric acid flowing into the electrode of Examples 1 to 4 is larger than that of Comparative Example 1.

Figure 7:
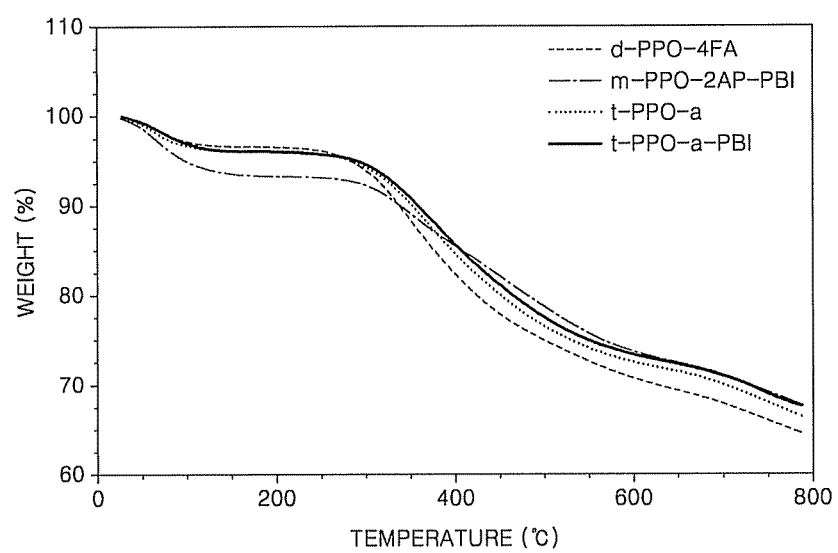
FIG. 7 is a graph illustrating the results of thermogravimetric analyses of t-PPO-a, d-PPO-4FA, a polymer of m-PPO-2AP and polybenzimidazole, and a polymer of t-PPO-a and polybenzimidazole.

Meanwhile, thermal stability of t-PPO-a, d-PPO-4FA, a polymer of m-PPO-2AP and polybenzimidazole, and a polymer of t-PPO-a and polybenzimidazole was measured using thermogravimetric analysis, and the results are shown in FIG. 7. The thermal weight loss was measured at 800° C. in FIG. 7. Referring to FIG. 7, t-PPO-a, d-PPO-4FA, a polymer of m-PPO-2AP and polybenzimidazole, and a polymer of t-PPO-a and polybenzimidazole had excellent thermal stability.

EXAMPLE 5

Preparation of an Electrolyte Membrane for a Fuel Cell and a Fuel Cell Using the Electrolyte Membrane To prepare the cathode, 1 g of a catalyst in which 50% by weight of PtCo is supported on carbon and 3 g of NMP as a solvent were added to a container, and the mixture was agitated using a mortar to prepare a slurry. A solution of 3% by weight of tBuPh-4FA according to Synthesis Example 1 and NMP was added to the slurry and stirred to provide 0.025 g of tBuPh-4FA.

Then, a solution of 5% by weight of polyvinylidenefluoride and NMP was added to the mixture to set the amount of the polyvinylidenefluoride to 0.025 g, and the mixture was mixed for 10 minutes to prepare a slurry for a cathode catalyst layer.

Carbon paper was cut into pieces of 4)(7 cm$^2$ in size, and the pieces were fixed on a glass plate and coated with the slurry using a doctor blade (Sheen instrument), wherein the gap interval of the doctor blade was 600 μm.

The slurry for a cathode catalyst layer was coated onto the carbon paper and dried at room temperature for 1 hour, at 80° C. for 1 hour, at 120° C. for 30 minutes and at 150° C. for 15 minutes to prepare a cathode (a fuel electrode). The amount of loaded Pt/Co in the prepared cathode was 2.32 mg/cm$^2$.

To prepare the anode, 2 g of a catalyst in which 50% by weight of Pt was loaded on carbon and 9 g of NMP solvent were added to a container, and the mixture was agitated in a high-speed agitator for 2 minutes.

Then, a solution of 0.05 g of polyvinylidenefluoride dissolved in 1 g of NMP was added thereto and agitated for 2 minutes to prepare a slurry for an anode catalyst layer. The slurry was coated using a bar coater onto carbon paper onto which a microporous layer had been previously coated. The amount of loaded Pt in the prepared anode was 1.44 mg/cm$^2$.

To prepare the electrolyte membrane, 65 parts by weight of t-PPO-a represented by Formula 13 and prepared in Synthesis Example 5 was blended with 35 parts by weight of polybenzimidazole (PBI), and the mixture was cured at about 220° C. Then, the resultant was impregnated with 85% by weight of phosphoric acid at 80° C. for longer than 4 hours to prepare an electrolyte membrane. The amount of phosphoric acid was about 530 parts by weight based on 100 parts by weight of the electrolyte membrane.

A membrane electrode assembly (MEA) was prepared by interposing the electrolyte membrane between the cathode and the anode. The cathode and anode were not impregnated with phosphoric acid.

A 200 μm thick TEFLON membrane for a main gasket and a 20 μm thick TEFLON membrane for a sub gasket were overlapped on an interface between the electrodes and electrolyte membrane in order to prevent gas permeation between the cathode and the anode. The pressure applied to the MEA was adjusted to 1, 2, 3 N-m torque step by step using a wrench to assemble a cell.

Characteristics of the fuel cell were measured while operating the fuel cell at 150° C. by supplying hydrogen to the anode at 100 ccm and supplying air to the cathode at 250 ccm. The electrolyte membrane was not hydrated. Since cell efficiency increases with time when using an electrolyte doped with phosphoric acid, the final efficiency was measured after the fuel cell was aged until the operational voltage was maximized. The area of the cathode and the anode was fixed to 7.84 cm$^2$ (2.8×2.8). The thickness of the cathode was about 430 μm, and the thickness of the anode was about 390 μm, although the thicknesses of the cathode and the anode varied according to the distribution of the carbon paper.

EXAMPLE 6

Preparation of an Electrolyte Membrane for a Fuel Cell and a Fuel Cell Using the Electrolyte Membrane An electrolyte membrane for a fuel cell and a fuel cell were prepared in the same manner as in Example 5, except that d-PPO-4FA represented by Formula 14 was used instead of t-PPO-a represented by Formula 13 in the preparation of the electrolyte membrane.

EXAMPLE 7

Preparation of an Electrolyte Membrane for a Fuel Cell and a Fuel Cell Using the Electrolyte Membrane An electrolyte membrane for a fuel cell and a fuel cell were prepared in the same manner as in Example 5, except that m-PPO-2AP represented by Formula 15 was used instead of t-PPO-a represented by Formula 13 in the preparation of the electrolyte membrane.

Figure 8:
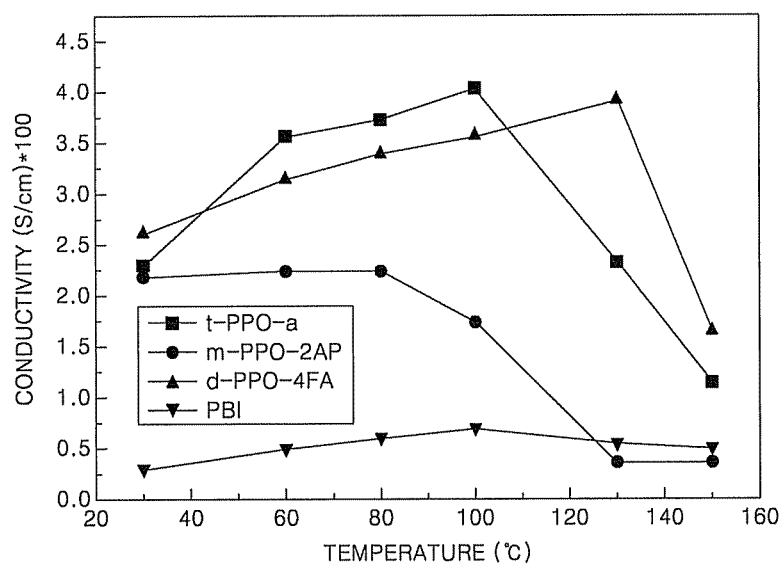
FIG. 8 is a graph illustrating conductivity with respect to temperature of electrolyte membranes prepared in Examples 5 to 7 and a polybenzimidazole electrolyte membrane.

Conductivity according to temperature was measured in electrolyte membranes prepared according to Examples 5 to 7, and the results are shown in FIG. 8.

Referring to FIG. 8, the electrolyte membranes prepared according to Examples 5 to 7 had greater conductivity than the electrolyte membrane prepared using PBI.

EXAMPLE 8

Preparation of an Electrolyte Membrane for a Fuel Cell and a Fuel Cell Using the Electrolyte Membrane An electrolyte membrane for a fuel cell and a fuel cell were prepared in the same manner as in Example 5, except that t-PPO-34DFA represented by Formula 9 was used instead of t-PPO-a represented by Formula 13 in the preparation of the electrolyte membrane.

Figure 9:
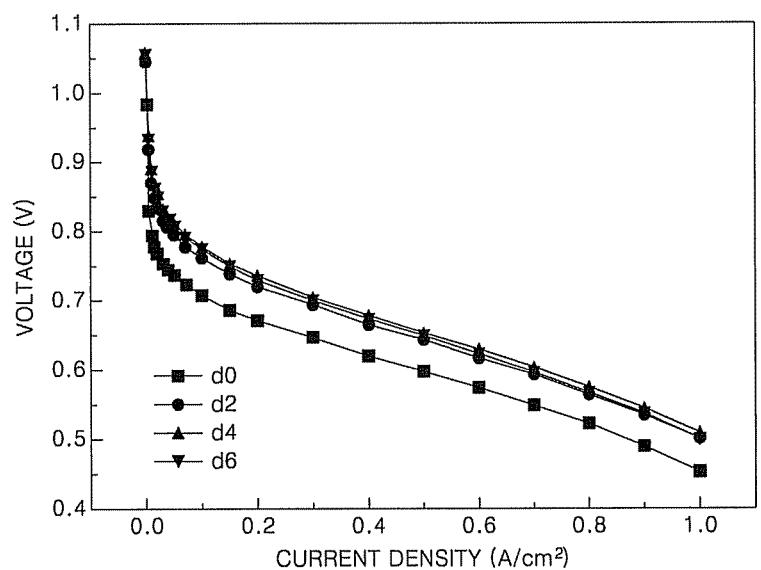
FIGS. 9 to 12 are graphs illustrating voltage with respect to current density of fuel cells prepared in Examples 5 to 8.
Figure 10:
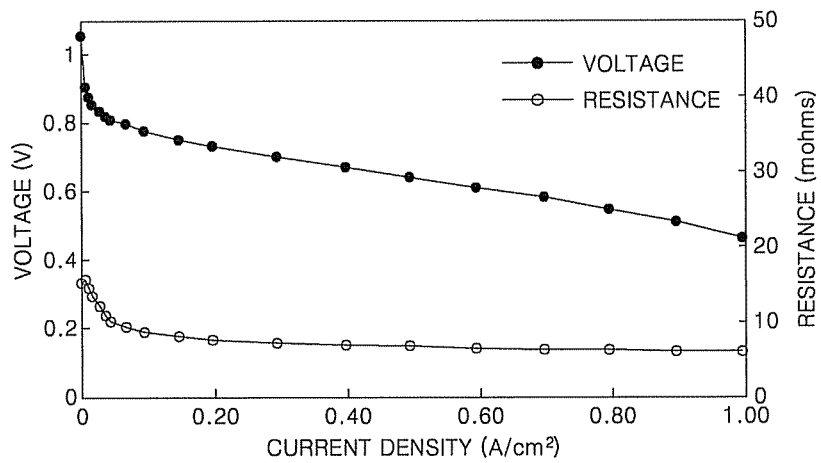
Figure 11:
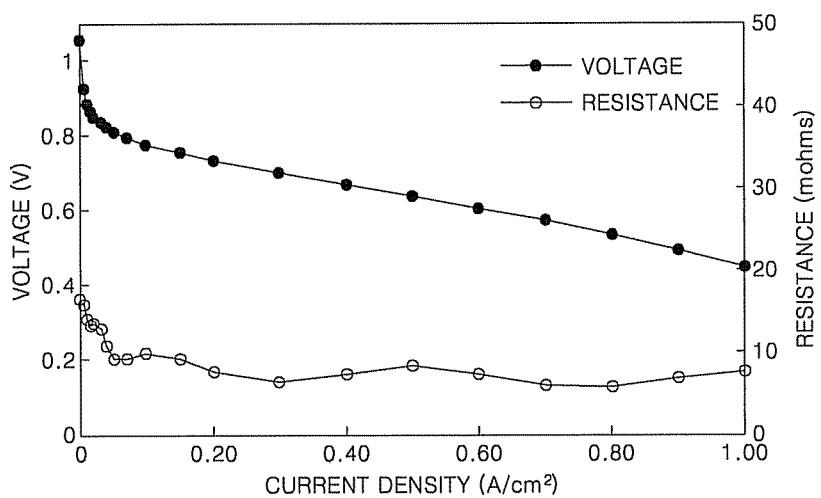
Figure 12:
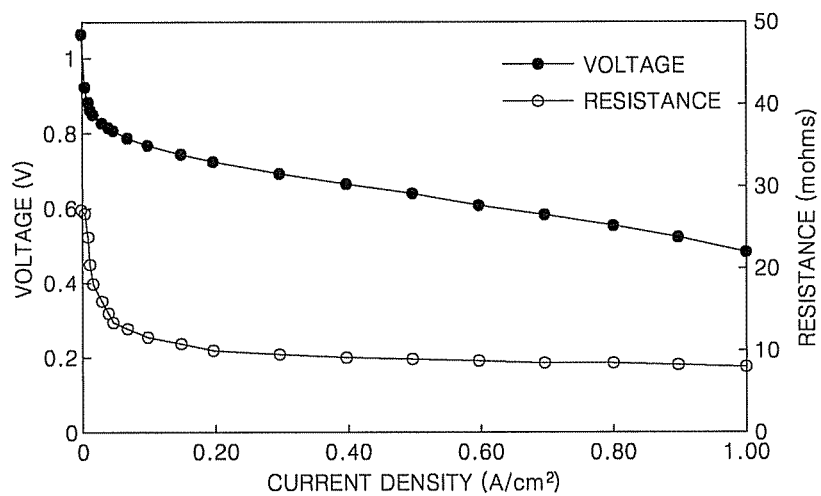

Cell voltage characteristics with respect to current density were measured in fuel cells prepared according to Examples 5 to 8, and the results are shown in FIGS. 9 and 12. In FIG. 9, d0 indicates voltage according to current density measured right after the fuel cell was assembled. The d2, d4, and d6 respectively indicate, second day, fourth day, and sixth day. As shown in FIG. 9, the fuel cells prepared according to Examples 5 to 8 had excellent cell voltage characteristics.

Figure 13:
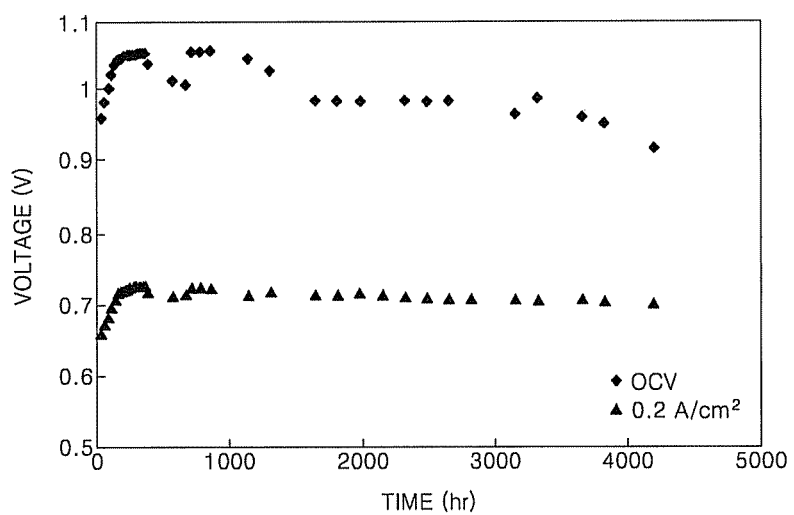
FIG. 13 is a graph illustrating cell voltage over time of a fuel cell prepared in Example 5.

Cell voltage over time was measured in the fuel cell prepared according to Example 5, and the results are shown in FIG. 13. In FIG. 13, "♦OCV" denotes an open circuit voltage (OCV), and "▲0.2 A/cm$^2$" denotes a cell voltage at a current density of 0.2 A/cm$^2$. Referring to FIG. 13, the fuel cell prepared according to Example 5 did not show voltage drop for 4500 hours.

Figure 14:
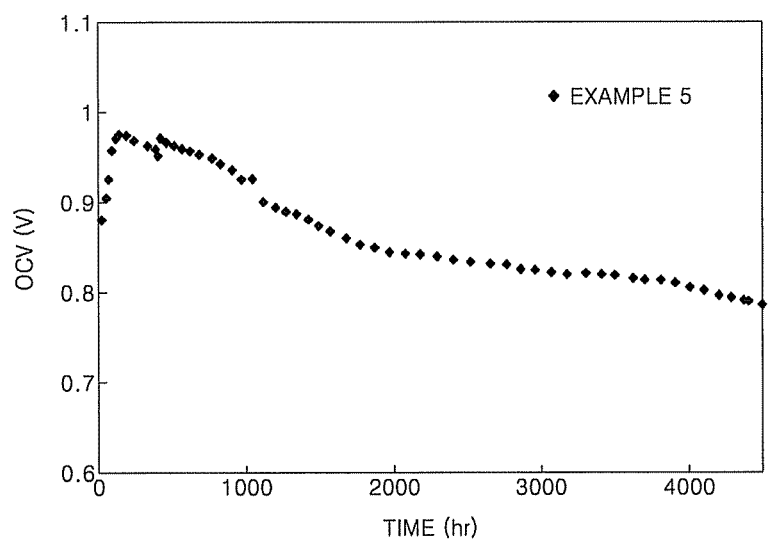
FIG. 14 is a graph illustrating accelerated lifetime characteristics of a fuel cell prepared in Example 5.
Figure 15:
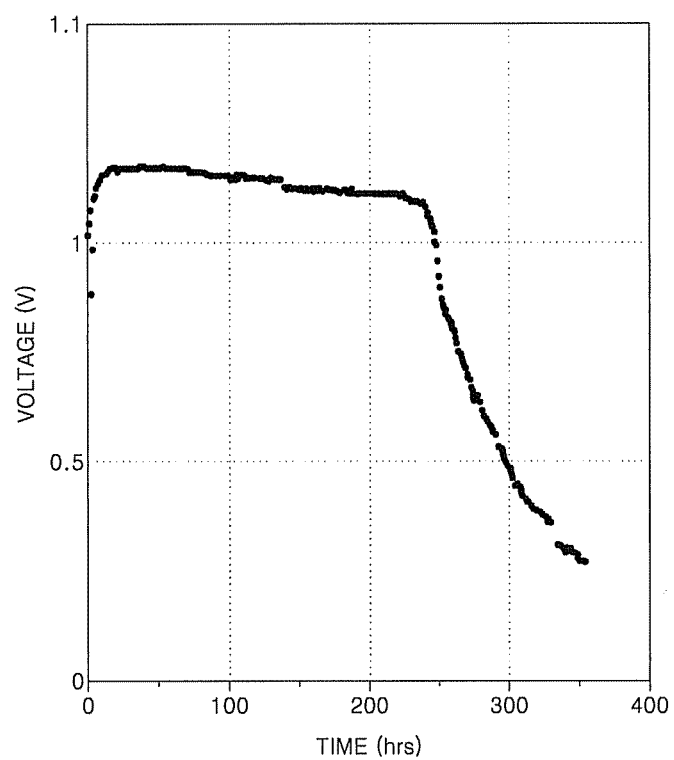
FIG. 15 is a graph illustrating accelerated lifetime characteristics of a fuel cell prepared using a PBI electrolyte membrane.

Accelerated lifetime characteristics of the fuel cell prepared according to Example 5 were evaluated, and the results are shown in FIG. 14. In this regard, the accelerated lifetime was measured by cycling current from 0 to 1 A/cm² once an hour. The accelerated lifetime of the fuel cell was compared with the accelerated lifetime of a fuel cell prepared using PBI electrolyte membrane as shown in FIG. 15. The cathode and anode of the fuel cell having the FBI membrane were prepared in the same manner as in Example 5 using PBI as the electrolyte membrane.

Referring to FIGS. 14 and 15, the fuel cell prepared in Example 5 had significantly improved accelerated lifetime when compared with the fuel cell prepared using the PBI electrolyte membrane.

EXAMPLE 9

Preparation of a Fuel Cell

To prepare the cathode, 1 g of a catalyst in which 50% by weight of PtCo was loaded on carbon and 3 g of NMP as a solvent were added to a container, and the mixture was agitated using a mortar to prepare a slurry. A solution of 10% by weight of a solution of t-PPO-a represented by Formula 12 and NMP was added to the slurry and agitated to provide 0.025 g of the compound represented by Formula 12.

Then, a solution of 5% by weight of polyvinylidenefluoride and NMP was added to the mixture to set the amount of the polyvinylidenefluoride to 0.025 g, and the mixture was mixed for 10 minutes to prepare a slurry for a cathode catalyst layer.

Carbon paper was cut into pieces of 4×7 cm² in size, and the pieces were fixed on a glass plate and coated with the slurry using a doctor blade (Sheen instrument), wherein the gap interval of the doctor blade was 600 μm.

The slurry for a cathode catalyst layer was coated onto the carbon paper and dried at room temperature for 1 hour, at 80° C. for 1 hour, at 120° C. for 30 minutes and at 150° C. for 15 minutes to prepare a cathode (a fuel electrode). The amount of loaded Pt/Co in the prepared cathode was 2.1 mg/cm².

To prepare the anode, 2 g of a catalyst in which 50% by weight of Pt is loaded on carbon and 9 g of NMP solvent were added to a container and the mixture was agitated in a high-speed agitator for 2 minutes. Then, a solution of 0.05 g of polyvinylidenefluoride dissolved in 1 g of NMP was added thereto and agitated for 2 minutes to prepare a slurry for an anode catalyst layer. The slurry was coated using a bar coater onto carbon paper onto which microporous layer had been previously coated. The amount of loaded Pt in the prepared anode was 1.34 mg/cm².

To prepare the electrolyte membrane, 65 parts by weight of d-PPO-4FA represented by Formula 13 was blended with 35 parts by weight of PSI, and the mixture was cured at about 220° C. Then, the resultant was impregnated with 85% by weight of phosphoric acid at 80° C. for longer than 4 hours to prepare an electrolyte membrane. The amount of phosphoric acid was about 472 parts by weight based on 100 parts by weight of electrolyte membrane.

A membrane electrode assembly (MEA) was prepared by interposing the electrolyte membrane between the cathode and the anode. The cathode and anode were not impregnated with phosphoric acid.

A 200 μm thick TEFLON membrane for a main gasket and a 20 μm thick TEFLON membrane for a sub gasket were overlapped on an interface between the electrodes and electrolyte membrane in order to prevent gas permeation between the cathode and the anode. The pressure applied to the MEA was adjusted to 1, 2, 3 N-m torque step by step using a wrench to assemble a cell.

Characteristics of the fuel cell were measured while operating the fuel cell at 150° C. by supplying hydrogen to the anode at 100 ccm and supplying air to the cathode at 250 ccm. The electrolyte membrane was not hydrated. Since cell efficiency increases with time when using an electrolyte doped with phosphoric acid, the final efficiency was measured after the fuel cell was aged until operational voltage was maximized. The area of the cathode and the anode was fixed to 7.84 cm² (2.8×2.8). The thickness of the cathode was about 430 μm, and the thickness of the anode was about 390 μm, although the thicknesses of the cathode and the anode varied according to the distribution of the carbon paper.

COMPARATIVE EXAMPLE 2

Preparation of a Fuel Cell

A fuel cell was prepared in the same manner as in Example 9, except that polybenzimidazole(PBI) was used as the electrolyte membrane instead of t-PPO-a represented by Formula 12 in the preparation of the cathode.

Figure 16:
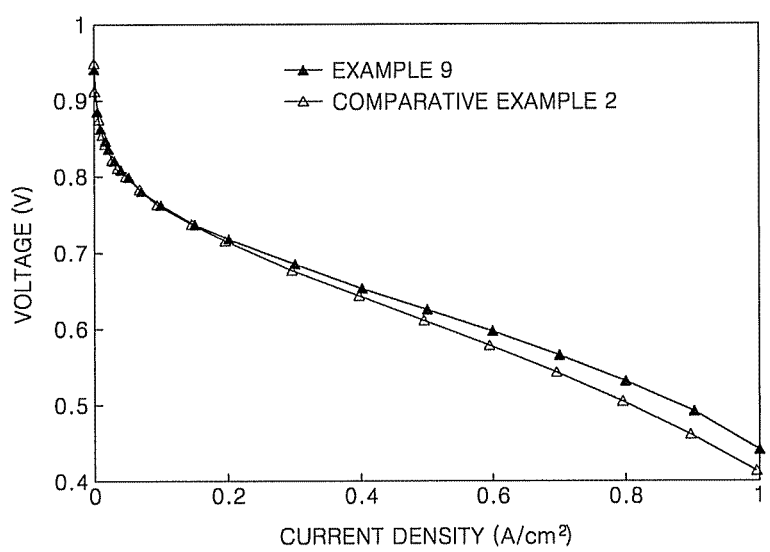
FIG. 16 is a graph illustrating voltage with respect to current density of fuel cells prepared in Example 9 and Comparative Examples 2.

Cell voltage characteristics with respect to current density of fuel cells prepared in Example 9 and Comparative Example 2 were measured, and the results are shown in FIG. 16.

Referring to FIG. 16, performance of the MEA prepared in Example 9 was improved compared with that of the MEA prepared in Comparative Example 2.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A phosphorous containing benzoxazine-based monomer selected from the group consisting of compounds represented by Formulae 2 and 3 below:

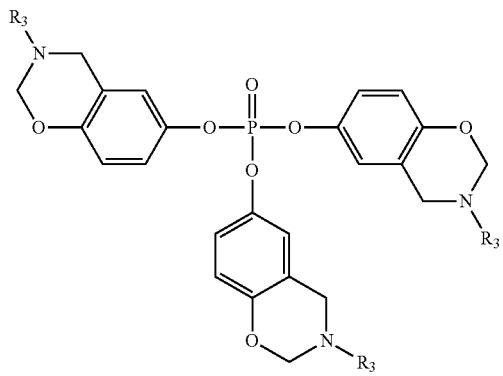

Formula 2

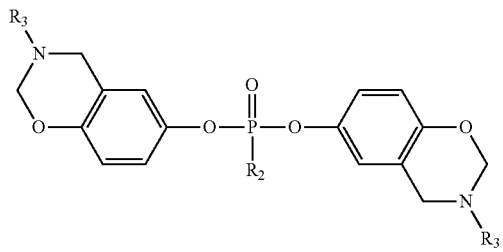

Formula 3 wherein $R_2$ is a C6- C10 aryloxy group, and
$R_3$ in Formulae 2 and 3 is selected from the groups represented by the formulae below:

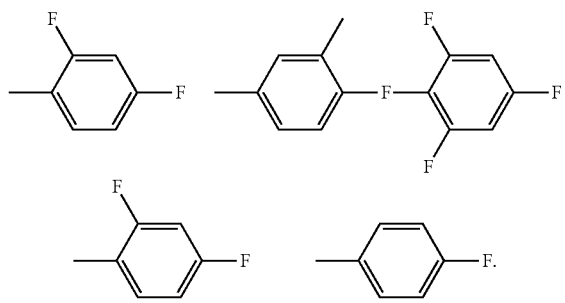

2. The phosphorous containing benzoxazine-based monomer of claim 1, wherein the monomer is a compound represented by Formula 13:

Formula 13

3. A polymer that is a polymerization product of a phosphorous containing benzoxazine-based monomer selected from the group consisting of compounds represented by Formulae 2 and 3 of claim 1,
or a polymerization product of a phosphorous containing benzoxazine-based
monomer selected from the group consisting of compounds represented by Formulae 2 and 3 and a crosslinkable compound.

4. The polymer of claim 3, wherein phosphorous containing benzoxazine-based monomer is a compound represented by Formula 13:

Formula 13

5. The polymer of claim 3, wherein the crosslinkable compound is at least one compound selected from the group consisting of polybenzimidazole (PBI), a polybenzimidazole-base complex, polybenzthiazole, polybenzoxazole, and polyimide.

6. The polymer of claim 5, wherein the amount of the crosslinkable compound is in the range of 5 to 95 parts by weight based on 100 parts by weight of the phosphorous containing benzoxazine-based monomer.

7. A phosphorus containing benzoxazine-based monomer represented by Formula 8:

Formula 8

* * * * *